United States Patent
McDermott et al.

(10) Patent No.: US 12,208,239 B2
(45) Date of Patent: Jan. 28, 2025

(54) FLUID INJECTOR SYSTEM, METHOD OF PREVENTING FLUID BACKFLOW, AND COMPUTER PROGRAM PRODUCT

(71) Applicant: BAYER HEALTHCARE LLC, Whippany, NJ (US)

(72) Inventors: Michael McDermott, Pittsburgh, PA (US); William Barone, Pittsburgh, PA (US); John Volkar, Valencia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 945 days.

(21) Appl. No.: 17/270,531

(22) PCT Filed: Aug. 27, 2019

(86) PCT No.: PCT/US2019/048249
§ 371 (c)(1),
(2) Date: Feb. 23, 2021

(87) PCT Pub. No.: WO2020/046869
PCT Pub. Date: Mar. 5, 2020

(65) Prior Publication Data
US 2021/0220556 A1 Jul. 22, 2021

Related U.S. Application Data

(60) Provisional application No. 62/723,739, filed on Aug. 28, 2018.

(51) Int. Cl.
*A61M 5/168* (2006.01)
*A61M 5/00* (2006.01)
(Continued)

(52) U.S. Cl.
CPC ...... *A61M 5/16827* (2013.01); *A61M 5/1422* (2013.01); *A61M 5/16854* (2013.01);
(Continued)

(58) Field of Classification Search
CPC ...... A61M 2205/3331; A61M 5/14546; A61M 5/16827; A61M 5/142; A61M 5/1407;
(Continued)

(56) References Cited

U.S. PATENT DOCUMENTS 383,858 A    6/1888   Campbell
508,584 A    11/1893  Stevens
(Continued)

FOREIGN PATENT DOCUMENTS

CA    2045070 A1    2/1992
CA    2077712 A1    12/1993
(Continued)

OTHER PUBLICATIONS

Behzadi et al, MR and CT contrast media extravasation., Medicine, 2018, 97, 9.
(Continued)

*Primary Examiner* — Michael J Tsai
*Assistant Examiner* — Nidah Hussain
(74) *Attorney, Agent, or Firm* — Joseph L. Kent; James R. Stevenson

(57) ABSTRACT

A fluid injector system and method for preventing pressurized backflow of a second fluid into a first reservoir containing a fluid is described. The fluid injector system includes a control device programmed or configured to actuate a second drive component to pressurize and inject the second fluid through the fluid conduit, and while the second drive component is actuated, actuate a first drive component to introduce intermittent pulses of the first fluid to create a flow front interface between the first fluid and the second fluid in the fluid conduit to prevent backflow of the second fluid through the fluid conduit into the first fluid reservoir.

21 Claims, 17 Drawing Sheets

(51) Int. Cl.
*A61M 5/14* (2006.01)
*A61M 5/142* (2006.01)

(52) U.S. Cl.
CPC ..... *A61M 5/007* (2013.01); *A61M 2005/1406* (2013.01); *A61M 2005/14208* (2013.01)

(58) Field of Classification Search
CPC .......... A61M 5/14; A61M 2005/14513; A61M 2005/14292; A61M 2005/14288; A61M 2005/14208; A61M 2005/1787; A61M 5/1422; A61M 5/16854; A61M 2005/1406
USPC ....................................................... 604/504
See application file for complete search history.

(56) References Cited

U.S. PATENT DOCUMENTS

| | | | |
|---|---|---|---|
| 945,143 | A | 1/1910 | Jacques |
| 2,511,291 | A | 6/1950 | Mueller |
| 2,583,206 | A | 1/1952 | Borck et al. |
| 3,156,236 | A | 11/1964 | Williamson |
| 3,159,312 | A | 12/1964 | Van Sciver, II |
| 3,276,472 | A | 10/1966 | Jinkens et al. |
| 3,349,713 | A | 10/1967 | Fassbender |
| 3,520,295 | A | 7/1970 | Kelly |
| 3,523,523 | A | 8/1970 | Heinrich et al. |
| 3,623,474 | A | 11/1971 | Heilman et al. |
| 3,635,444 | A | 1/1972 | Potter |
| 3,671,208 | A | 6/1972 | Medsker |
| 3,701,345 | A | 10/1972 | Heilman |
| 3,719,207 | A | 3/1973 | Takeda |
| 3,755,655 | A | 8/1973 | Senecal |
| 3,769,976 | A * | 11/1973 | Victory ................ A61M 3/022 604/150 |
| 3,793,600 | A | 2/1974 | Grosbard |
| 3,812,843 | A | 5/1974 | Wootten et al. |
| 3,817,843 | A | 6/1974 | Barrett |
| 3,839,708 | A | 10/1974 | Lyons et al. |
| 3,868,967 | A | 3/1975 | Harding |
| 3,888,239 | A | 6/1975 | Rubinstein |
| 3,895,220 | A | 7/1975 | Nelson et al. |
| 3,898,983 | A | 8/1975 | Elam |
| 3,927,955 | A | 12/1975 | Spinosa et al. |
| 3,941,126 | A | 3/1976 | Dietrich et al. |
| 3,958,103 | A | 5/1976 | Oka et al. |
| 3,968,195 | A | 7/1976 | Bishop |
| 3,995,381 | A | 12/1976 | Manfred et al. |
| 4,001,549 | A | 1/1977 | Corwin |
| 4,006,736 | A | 2/1977 | Kranys et al. |
| 4,038,981 | A | 8/1977 | Lefevre et al. |
| 4,044,757 | A | 8/1977 | McWhorter et al. |
| 4,090,502 | A | 5/1978 | Tajika |
| 4,135,247 | A | 1/1979 | Gordon et al. |
| 4,151,845 | A | 5/1979 | Clemens |
| 4,187,057 | A | 2/1980 | Xanthopoulos |
| 4,191,183 | A | 3/1980 | Mendelson |
| 4,199,000 | A | 4/1980 | Edstrom |
| 4,204,775 | A | 5/1980 | Speer |
| 4,207,871 | A | 6/1980 | Jenkins |
| 4,208,136 | A | 6/1980 | King et al. |
| 4,223,675 | A | 9/1980 | Williams |
| 4,262,824 | A | 4/1981 | Hrynewycz |
| 4,263,916 | A | 4/1981 | Brooks et al. |
| 4,280,494 | A | 7/1981 | Cosgrove, Jr. et al. |
| 4,284,073 | A | 8/1981 | Krause et al. |
| 4,315,247 | A | 2/1982 | Germanton |
| 4,319,568 | A | 3/1982 | Tregoning |
| 4,329,067 | A | 5/1982 | Goudy, Jr. |
| 4,340,153 | A | 7/1982 | Spivey |
| 4,341,153 | A | 7/1982 | Bowser |
| 4,392,847 | A | 7/1983 | Whitney et al. |
| 4,392,849 | A | 7/1983 | Petre et al. |
| 4,396,385 | A | 8/1983 | Kelly et al. |
| 4,402,310 | A | 9/1983 | Kimura |
| 4,409,966 | A | 10/1983 | Lambrecht et al. |
| 4,434,820 | A | 3/1984 | Glass |
| 4,434,822 | A | 3/1984 | Bellamy et al. |
| 4,441,823 | A | 4/1984 | Power et al. |
| 4,444,198 | A | 4/1984 | Petre |
| 4,447,230 | A | 5/1984 | Gula et al. |
| 4,448,200 | A | 5/1984 | Brooks et al. |
| 4,474,476 | A | 10/1984 | Thomsen |
| 4,477,923 | A | 10/1984 | Baumann et al. |
| 4,479,760 | A | 10/1984 | Bilstad et al. |
| 4,479,761 | A | 10/1984 | Bilstad et al. |
| 4,479,762 | A | 10/1984 | Bilstad et al. |
| 4,504,908 | A | 3/1985 | Riederer et al. |
| 4,509,526 | A | 4/1985 | Barnes et al. |
| 4,512,764 | A | 4/1985 | Wunsch |
| 4,542,459 | A | 9/1985 | Riederer |
| 4,544,949 | A | 10/1985 | Kurihara |
| 4,551,133 | A | 11/1985 | Zegers et al. |
| 4,552,130 | A | 11/1985 | Kinoshita |
| 4,559,036 | A | 12/1985 | Wunsch |
| 4,563,175 | A | 1/1986 | Lafond |
| 4,578,802 | A | 3/1986 | Itoh |
| 4,585,009 | A | 4/1986 | Barker et al. |
| 4,585,941 | A | 4/1986 | Bergner |
| 4,610,665 | A | 9/1986 | Matsumoto et al. |
| 4,610,670 | A | 9/1986 | Spencer |
| 4,610,790 | A | 9/1986 | Reti et al. |
| 4,611,340 | A | 9/1986 | Okazaki |
| 4,612,572 | A | 9/1986 | Komatsu et al. |
| 4,625,494 | A | 12/1986 | Iwatschenko et al. |
| 4,626,144 | A | 12/1986 | Berner |
| 4,633,307 | A | 12/1986 | Honda |
| 4,634,426 | A | 1/1987 | Kamen |
| 4,636,144 | A | 1/1987 | Abe et al. |
| 4,655,197 | A | 4/1987 | Atkinson |
| 4,662,906 | A | 5/1987 | Matkovich et al. |
| 4,672,651 | A | 6/1987 | Horiba et al. |
| 4,676,776 | A | 6/1987 | Howson |
| 4,682,170 | A | 7/1987 | Kubota et al. |
| 4,689,670 | A | 8/1987 | Okazaki |
| 4,710,166 | A | 12/1987 | Thompson et al. |
| 4,723,261 | A | 2/1988 | Janssen et al. |
| 4,750,643 | A | 6/1988 | Wortrich |
| 4,754,786 | A | 7/1988 | Roberts |
| 4,781,687 | A | 11/1988 | Wall |
| 4,783,273 | A | 11/1988 | Knutsson et al. |
| 4,789,014 | A | 12/1988 | DiGianfilippo et al. |
| 4,793,357 | A | 12/1988 | Lindstrom |
| 4,795,429 | A | 1/1989 | Feldstein |
| 4,798,590 | A | 1/1989 | O'Leary et al. |
| 4,804,454 | A | 2/1989 | Asakura et al. |
| 4,823,833 | A | 4/1989 | Hogan et al. |
| 4,835,521 | A | 5/1989 | Andrejasich et al. |
| 4,836,187 | A | 6/1989 | Iwakoshi et al. |
| 4,838,856 | A | 6/1989 | Mulreany et al. |
| 4,840,620 | A | 6/1989 | Kobayashi et al. |
| 4,844,052 | A | 7/1989 | Iwakoshi et al. |
| 4,853,521 | A | 8/1989 | Claeys et al. |
| 4,854,301 | A | 8/1989 | Nakajima |
| 4,854,324 | A | 8/1989 | Hirschman et al. |
| 4,857,056 | A | 8/1989 | Talonn |
| 4,874,359 | A | 10/1989 | White et al. |
| 4,879,880 | A | 11/1989 | Harrison |
| 4,880,014 | A | 11/1989 | Zarowitz et al. |
| 4,887,208 | A | 12/1989 | Schneider et al. |
| 4,887,554 | A | 12/1989 | Whitford |
| 4,901,731 | A | 2/1990 | Millar |
| 4,903,705 | A | 2/1990 | Imamura et al. |
| 4,913,154 | A | 4/1990 | Ermert et al. |
| 4,922,916 | A | 5/1990 | Ermert et al. |
| 4,925,444 | A | 5/1990 | Orkin et al. |
| 4,929,818 | A | 5/1990 | Bradbury et al. |
| 4,935,005 | A | 6/1990 | Haines |
| 4,936,832 | A | 6/1990 | Vaillancourt |
| 4,943,279 | A | 7/1990 | Samiotes et al. |
| 4,943,779 | A | 7/1990 | Pedersen et al. |
| 4,943,987 | A | 7/1990 | Asahina et al. |
| 4,946,256 | A | 8/1990 | Woodruff |
| 4,946,439 | A | 8/1990 | Eggers |
| 4,947,412 | A | 8/1990 | Mattson |

(56) References Cited

U.S. PATENT DOCUMENTS

| | | |
|---|---|---|
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,026,348 A | 6/1991 | Venegas |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,163,928 A | 11/1992 | Hobbs et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | MacVicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,651,776 A | 7/1997 | Appling et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |

(56) References Cited

U.S. PATENT DOCUMENTS

| | | |
|---|---|---|
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,954,668 A | 9/1999 | Uber, III et al. |
| 5,964,703 A | 10/1999 | Goodman et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,159,183 A | 12/2000 | Neer et al. |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,375,624 B1 | 4/2002 | Uber, III et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,408,204 B1 | 6/2002 | Hirschman |
| 6,423,719 B1 | 7/2002 | Lawyer |
| 6,442,418 B1 | 8/2002 | Evans, III et al. |
| 6,459,931 B1 | 10/2002 | Hirschman |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,751,500 B2 | 6/2004 | Hirschman |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,047,058 B1 | 5/2006 | Dvorsky et al. |
| 7,094,216 B2 | 8/2006 | Trombley, III et al. |
| 7,122,012 B2 | 10/2006 | Bouton et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley et al. |
| 7,427,281 B2 | 9/2008 | Uber et al. |
| 7,553,294 B2 | 6/2009 | Lazzaro et al. |
| 7,553,295 B2 | 6/2009 | Susi |
| 7,556,619 B2 | 7/2009 | Spohn et al. |
| 7,563,249 B2 | 7/2009 | Schriver et al. |
| 7,591,792 B2 | 9/2009 | Bouton |
| 7,666,169 B2 | 2/2010 | Cowan et al. |
| 7,688,057 B2 | 3/2010 | Foss et al. |
| 7,766,883 B2 | 8/2010 | Reilly et al. |
| 7,861,893 B2 | 1/2011 | Voegele et al. |
| 7,925,330 B2 | 4/2011 | Kalafut et al. |
| 7,937,134 B2 | 5/2011 | Uber et al. |
| 8,007,487 B2 | 8/2011 | Patrick et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,235,949 B2 | 8/2012 | Hack et al. |
| 8,295,914 B2 | 10/2012 | Kalafut et al. |
| 8,295,920 B2 | 10/2012 | Bouton et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,540,698 B2 | 9/2013 | Spohn et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,289,550 B1 | 3/2016 | Dvorsky et al. |
| 9,314,749 B2 | 4/2016 | Yagi et al. |
| 9,326,686 B2 | 5/2016 | Warren et al. |
| 9,333,293 B2 | 5/2016 | Williams, Jr. et al. |
| 9,474,857 B2 * | 10/2016 | Riley ............... A61M 5/16827 |
| 9,480,788 B2 | 11/2016 | Wagner |
| 9,480,791 B2 | 11/2016 | Reilly |
| 9,555,379 B2 | 1/2017 | Schriver et al. |
| 9,566,381 B2 | 2/2017 | Barron et al. |
| 9,855,387 B2 | 1/2018 | Small et al. |
| 9,861,752 B2 | 1/2018 | Buder et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,124,110 B2 | 11/2018 | Dedig et al. |
| 10,201,666 B2 | 2/2019 | Cowan et al. |
| D847,985 S | 5/2019 | Neff et al. |
| 10,398,353 B2 | 9/2019 | Addison et al. |
| 10,507,319 B2 | 12/2019 | Haury et al. |
| 10,549,084 B2 | 2/2020 | Sokolov et al. |
| 10,583,256 B2 | 3/2020 | Berry et al. |
| 10,898,638 B2 | 1/2021 | Spohn et al. |
| 10,933,190 B2 | 3/2021 | Berry et al. |
| 11,141,535 B2 | 10/2021 | Uber, III et al. |
| 11,478,581 B2 | 10/2022 | McDermott et al. |
| 2001/0018937 A1 | 9/2001 | Nemoto |
| 2001/0027265 A1 | 10/2001 | Prince |
| 2001/0056233 A1 | 12/2001 | Uber et al. |
| 2002/0007116 A1 | 1/2002 | Zatezalo et al. |
| 2002/0010551 A1 | 1/2002 | Wang et al. |
| 2002/0099254 A1 | 7/2002 | Movahed |
| 2002/0123702 A1 | 9/2002 | Cho |
| 2002/0151854 A1 | 10/2002 | Duchon et al. |
| 2003/0050556 A1 | 3/2003 | Uber et al. |

(56) References Cited

U.S. PATENT DOCUMENTS

| | | |
|---|---|---|
| 2003/0120171 A1 | 6/2003 | Diamantopoulos et al. |
| 2003/0195462 A1 | 10/2003 | Mann et al. |
| 2003/0212364 A1 | 11/2003 | Mann et al. |
| 2003/0216683 A1 | 11/2003 | Shekalim |
| 2003/0226539 A1 | 12/2003 | Kim et al. |
| 2004/0011740 A1 | 1/2004 | Bernard et al. |
| 2004/0025452 A1 | 2/2004 | McLean |
| 2004/0044302 A1 | 3/2004 | Bernard et al. |
| 2004/0092905 A1 | 5/2004 | Azzolini |
| 2004/0097806 A1 | 5/2004 | Hunter et al. |
| 2004/0154788 A1 | 8/2004 | Symonds |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0171923 A1 | 9/2004 | Kalafut et al. |
| 2004/0215144 A1 | 10/2004 | Duchon et al. |
| 2004/0253183 A1 | 12/2004 | Uber, III et al. |
| 2005/0107697 A1 | 5/2005 | Berke et al. |
| 2005/0113766 A1 | 5/2005 | Mottola et al. |
| 2005/0171487 A1 | 8/2005 | Haury et al. |
| 2005/0234428 A1 | 10/2005 | Spohn et al. |
| 2006/0052794 A1 | 3/2006 | McGill et al. |
| 2006/0079765 A1 | 4/2006 | Neer et al. |
| 2006/0079843 A1 | 4/2006 | Brooks et al. |
| 2006/0135940 A1* | 6/2006 | Joshi ............... A61M 5/172 604/890.1 |
| 2006/0167415 A1 | 7/2006 | Nemoto |
| 2006/0173360 A1 | 8/2006 | Kalafut et al. |
| 2006/0211970 A1 | 9/2006 | Sciulli |
| 2007/0068964 A1 | 3/2007 | Tanaami et al. |
| 2007/0129705 A1 | 6/2007 | Trombley et al. |
| 2007/0161970 A1 | 7/2007 | Spohn et al. |
| 2007/0219496 A1 | 9/2007 | Kamen et al. |
| 2007/0276327 A1 | 11/2007 | Kalafut et al. |
| 2008/0015406 A1 | 1/2008 | Dlugos et al. |
| 2008/0045925 A1 | 2/2008 | Stepovich et al. |
| 2008/0147147 A1 | 6/2008 | Griffiths et al. |
| 2008/0167621 A1 | 7/2008 | Wagner et al. |
| 2008/0183131 A1 | 7/2008 | Duchon et al. |
| 2009/0216192 A1 | 8/2009 | Schriver et al. |
| 2009/0234226 A1 | 9/2009 | Nemoto |
| 2009/0247865 A1 | 10/2009 | Spohn et al. |
| 2009/0247961 A1 | 10/2009 | Carlyon |
| 2009/0312744 A1 | 12/2009 | Keeley et al. |
| 2010/0113887 A1 | 5/2010 | Kalafut et al. |
| 2010/0114064 A1 | 5/2010 | Kalafut et al. |
| 2010/0130809 A1 | 5/2010 | Morello |
| 2010/0249586 A1 | 9/2010 | Cocker et al. |
| 2010/0262078 A1 | 10/2010 | Blomquist |
| 2010/0331779 A1 | 12/2010 | Nystrom et al. |
| 2011/0275988 A1 | 11/2011 | Davis et al. |
| 2012/0089114 A1 | 4/2012 | Hemond et al. |
| 2012/0101472 A1 | 4/2012 | Schroeder et al. |
| 2012/0123229 A1 | 5/2012 | Butterfield et al. |
| 2012/0178629 A1 | 7/2012 | Hudson et al. |
| 2012/0203177 A1 | 8/2012 | Lanier, Jr. et al. |
| 2012/0204997 A1 | 8/2012 | Winn et al. |
| 2012/0217231 A1 | 8/2012 | Moore et al. |
| 2012/0245560 A1 | 9/2012 | Hochman |
| 2013/0030290 A1 | 1/2013 | Nemoto |
| 2013/0123619 A1 | 5/2013 | Griggs |
| 2013/0245439 A1 | 9/2013 | Small et al. |
| 2013/0245604 A1 | 9/2013 | Kouyoumjian et al. |
| 2013/0261993 A1 | 10/2013 | Ruchti et al. |
| 2013/0274599 A1 | 10/2013 | Bouton et al. |
| 2014/0142537 A1 | 5/2014 | Gibson et al. |
| 2014/0276550 A1 | 9/2014 | Uram et al. |
| 2016/0030662 A1 | 2/2016 | Uber, III et al. |
| 2016/0224750 A1 | 8/2016 | Kethman et al. |
| 2016/0278725 A1 | 9/2016 | Van Nijnatten |
| 2016/0331896 A1 | 11/2016 | Nemoto et al. |
| 2016/0346485 A1 | 12/2016 | Mohr et al. |
| 2017/0035974 A1 | 2/2017 | Berry et al. |
| 2017/0056603 A1 | 3/2017 | Cowan et al. |
| 2017/0100534 A1 | 4/2017 | Fukikoshi et al. |
| 2017/0112995 A1 | 4/2017 | Sams et al. |
| 2017/0136424 A1* | 5/2017 | Schriver ........... B01F 25/43141 |
| 2017/0143898 A1 | 5/2017 | Grosse-Wentrup et al. |
| 2017/0196702 A1* | 7/2017 | Agarwal ............... A61F 2/4601 |
| 2017/0232173 A1 | 8/2017 | Perry et al. |
| 2017/0258982 A1 | 9/2017 | Kemper |
| 2017/0290971 A1 | 10/2017 | Hedmann et al. |
| 2017/0312430 A1 | 11/2017 | Schleicher et al. |
| 2017/0343446 A1 | 11/2017 | Ciolkosz et al. |
| 2017/0361017 A1 | 12/2017 | Verma et al. |
| 2018/0015274 A1* | 1/2018 | Haury ............... A61M 5/14212 |
| 2018/0133392 A1 | 5/2018 | Dembo et al. |
| 2018/0161496 A1 | 6/2018 | Berry et al. |
| 2018/0261496 A1 | 9/2018 | Liu et al. |
| 2018/0280630 A1 | 10/2018 | Jiang et al. |
| 2018/0296755 A1 | 10/2018 | Dahlin et al. |
| 2019/0134297 A1 | 5/2019 | Kamen et al. |
| 2019/0201082 A1* | 7/2019 | Shelton, IV ............ A61M 1/74 |
| 2020/0035355 A1 | 1/2020 | Xavier et al. |
| 2020/0114074 A1 | 4/2020 | Barone et al. |
| 2020/0129702 A1 | 4/2020 | Pedersen |
| 2020/0146647 A1 | 5/2020 | Uber, III et al. |
| 2020/0149948 A1 | 5/2020 | McDermott et al. |
| 2020/0179595 A1 | 6/2020 | Mcdermott et al. |
| 2020/0206414 A1 | 7/2020 | Marsh et al. |
| 2020/0246541 A1 | 8/2020 | Neftel et al. |
| 2021/0146063 A1 | 5/2021 | Mcdermott et al. |
| 2021/0220557 A1 | 7/2021 | Chaya et al. |
| 2021/0338922 A1 | 11/2021 | Uber, III et al. |
| 2022/0001092 A1 | 1/2022 | Benamou et al. |
| 2024/0131268 A1 | 4/2024 | Uber, III et al. |

FOREIGN PATENT DOCUMENTS

| | | |
|---|---|---|
| CA | 2234050 A1 | 4/1997 |
| CN | 1671428 A | 9/2005 |
| CN | 103347552 A | 10/2013 |
| DE | 3203594 A1 | 8/1983 |
| DE | 3726452 A1 | 2/1989 |
| DE | 4426387 A1 | 8/1995 |
| DE | 19702896 A1 | 7/1997 |
| DE | 19647701 A1 | 5/1998 |
| DE | 19919572 A1 | 11/2000 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A1 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0439711 B1 | 5/1995 |
| EP | 0869738 A1 | 10/1998 |
| EP | 1016427 A2 | 7/2000 |
| EP | 1800704 A1 | 6/2007 |
| EP | 2692375 A1 | 2/2014 |
| EP | 2990073 A1 | 3/2016 |
| EP | 1838365 B1 | 2/2019 |
| FR | 2493708 A1 | 5/1982 |
| FR | 2561949 A1 | 10/1985 |
| GB | 201800 A | 8/1923 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | 860194935 A | 10/1985 |
| JP | S60194934 A | 10/1985 |
| JP | S60253197 A | 12/1985 |

(56) References Cited

FOREIGN PATENT DOCUMENTS

| | | |
|---|---|---|
| JP | S62216199 A | 9/1987 |
| JP | 86340538 A | 2/1988 |
| JP | S63290547 A | 11/1988 |
| JP | 01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H0849598 A | 2/1996 |
| JP | H0999034 A | 4/1997 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004236849 A | 8/2004 |
| JP | 2004298550 A | 10/2004 |
| JP | 4960180 B2 | 6/2012 |
| JP | 5063593 B2 | 10/2012 |
| JP | 5203971 B2 | 6/2013 |
| JP | 5227791 B2 | 7/2013 |
| JP | 5485885 B2 | 5/2014 |
| JP | 5490840 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6618673 B2 | 12/2019 |
| JP | 6644469 B2 | 2/2020 |
| JP | 6676377 B2 | 4/2020 |
| JP | 6792104 B2 | 11/2020 |
| JP | 6839853 B2 | 3/2021 |
| NO | 2014049656 A1 | 4/2014 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 0141835 A2 | 6/2001 |
| WO | 03015633 A1 | 2/2003 |
| WO | 2004012787 A2 | 2/2004 |
| WO | 2004035116 A1 | 4/2004 |
| WO | 2004091688 A2 | 10/2004 |
| WO | 2005016165 A1 | 2/2005 |
| WO | 2005035995 A1 | 4/2005 |
| WO | 2006042093 A1 | 4/2006 |
| WO | 2006074415 A1 | 7/2006 |
| WO | 2007079016 A2 | 7/2007 |
| WO | 2007092618 A2 | 8/2007 |
| WO | 2007116840 A1 | 10/2007 |
| WO | 2007116862 A1 | 10/2007 |
| WO | 2007116891 A1 | 10/2007 |
| WO | 2007133942 A2 | 11/2007 |
| WO | 2008078604 A1 | 7/2008 |
| WO | 2008106108 A1 | 9/2008 |
| WO | 2008153831 A2 | 12/2008 |
| WO | 2009026420 A1 | 2/2009 |
| WO | 2009042577 A2 | 4/2009 |
| WO | 2009051995 A1 | 4/2009 |
| WO | 2010027636 A1 | 3/2010 |
| WO | 2010117841 A1 | 10/2010 |
| WO | 2011002744 A1 | 1/2011 |
| WO | 2011011346 A1 | 1/2011 |
| WO | 2011097487 A2 | 8/2011 |
| WO | 2011125303 A1 | 10/2011 |
| WO | 2012048277 A2 | 4/2012 |
| WO | 2012155035 A1 | 11/2012 |
| WO | 2013043868 A1 | 3/2013 |
| WO | 2014035672 A2 | 3/2014 |
| WO | 2014144651 A2 | 9/2014 |
| WO | 2014179326 A1 | 11/2014 |
| WO | 2014190264 A1 | 11/2014 |
| WO | 2015106107 A1 | 7/2015 |
| WO | 2015164783 A1 | 10/2015 |
| WO | 2016004329 A1 | 1/2016 |
| WO | 2016112163 A1 | 7/2016 |
| WO | 2016172467 A1 | 10/2016 |
| WO | 2016191485 A1 | 12/2016 |
| WO | 2017012781 A1 | 1/2017 |
| WO | 2017038575 A1 | 3/2017 |
| WO | 2017096072 A1 | 6/2017 |
| WO | 2017152036 A1 | 9/2017 |
| WO | 2018060505 A1 | 4/2018 |
| WO | 2018075379 A1 | 4/2018 |
| WO | 2018075386 A1 | 4/2018 |
| WO | 2018089882 A1 | 5/2018 |
| WO | 2018144369 A1 | 8/2018 |
| WO | 2019046299 A1 | 3/2019 |
| WO | 2019204605 A1 | 10/2019 |
| WO | 2020046869 A1 | 3/2020 |

OTHER PUBLICATIONS

Angiography, Catheterization and Cardiovascular Diagnosis, vol. 19, pp. 123-128, 1990.

"International Preliminary Report on Patentability from PCT Application No. PCT/US2019/048249", Mar. 11, 2021.

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al."Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium volume achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

(56) References Cited

OTHER PUBLICATIONS

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).
"Digital Injector for Angiography", Sias. (Sep. 7, 1993).
Disposable Low-Cost Catheter Tip Sensor Measures Blood Pressure during Surgery, Sensor (Jul. 1989).
EZ Chem Brochure, E-Z-EM, Inc. (Jul. 2007).
Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.
Flegal, K.M., et al., "Prevalence and trends in obesity among US adults," JAMA, 2002, vol. 288, Issue 14, pp. 1-4, (1999-2000).
Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).
Fleischmann, D., "Contrast Medium Injection Technique," In: U. Joseph Schoepf: "Multidetector—Row CT of the Thorax," pp. 47-59 (Jan. 22, 2004).
Fleischmann, D., "Present and Future Trends in Multiple Detector—Row CT Applications; CT Angiography", European Radiology, vol. 12, Issue 2, Supplement 2, Jul. 2002, pp. s11-s15.
Gardiner, G. A., et al., "Selective Coronary Angiography Using a Power Injector," AJR Am J Roentgenol., vol. 146, Issue 4, pp. 831-833 (Apr. 1986).
Garrett, J. S., et al., "Measurement of cardiac output by cine computed tomography," The American Journal of Cardiology, vol. 56, Issue 10, pp. 657-661, 1985.
Gembicki, F.W., "Vector Optimization for Control with Performance and Parameter Sensitivity Indices," PhD Thesis Case Western Reserve University, 1974.
Gentilini A., et al., "A new paradigm for the closed-loop intraoperative administration of analgesics in humans," IEEE Transactions on Biomedical Engineering, vol. 49, Issue 4, pp. 289-299 (Apr. 2002).
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).
Tackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-555, 1987.
Harris P., H. D. "The Human Pulmonary Circulation," Edinburgh, Churchill Livingstone, (Appendix I), 1986.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).

Ireland, M.A., et al., "Safety and Convenience of a Mechanical Injector Pump for Coronary Angiography, "Catheterization and Cardiovascular Diagnosis, vol. 16, Issue 3, pp. 199-201 (1989).
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Liebel-Flarsheim Company, "Angiomat 6000 Digital Injection System-Operator's Manual", Document No. 600950, Rev. 1, Jan. 1990.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Mark V/Mark V Plus Injector Operation Manual KMP 805P Rev. B. MEDRAD, Inc, 1990.
McClellan, J.H., "Parametric Signal Modeling," Chapter 1 in Advanced Topics in Signal Processing, Pentice-Hall, Englewood Cliffs, NJ (1988).
MCT and MCT Plus Injection Systems Operation Manual KMP 810P, MEDRAD, Inc, 1991.
Morden Peter.; et al, "The Role of Saline Flush Injection Rate in Displacement of CT Injectable Peripherally Inserted Central Catheter Tip During Power Injection of Contrast Material", AJR, Jan. 2014, 202, W13-W18.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
Brenner et al, Radiation Exposure From Medical Imaging: Time to Regulate?, JAMA, Jul. 14, 2010, vol. 304 No 2, 208-209.
Extravasation Sensor Support System LD Operation Manual, Nemoto Kyorindo Co Ltd, Sep. 13, 2012, Rev 4.
Kern et al, Multi-Sensor Activity Context Detection for Wearable Computing, 2016.
McCullough, et al., "Risk Prediction of Contrast-Induced Nephropathy", The American Journal of Cardiology, Sep. 18, 2006, vol. 98.
Sachiko T. Cochran et al., Trends in Adverse Events After IV Administration of Contrast Media, Am. J. of Roentgenology, Jun. 2001, 176, 1385-1388.
Shaqdan et al, Incidence of contrast medium extravastion for CT and MRI in a large academic medical centre: A report on 502,391 injections, Clinical Radiology, Elsevier, 2014, 69, 1264-1272.
"The Solution for Our IV Formulas", IV 6500 Formulator Volumetric Pump, Valley Lab Inc., 39C 9410976 0000071 s, E-39-15, pp. 3399-3400, As early as 1980.
Vinod et al, Acute compartment syndrome of hand resulting from radiograph contrast iohexol exravasation, Journal of Pharmacology and Pharmacotherapeutics, 2016, 44-7, 7-44.
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Contrast Agent With Potential For Ultrasound Imaging of Liver," Ultrasound in Medicine & Biology, vol. 13, Issue 9, pp. 555-566 (Sep. 1987).

(56) References Cited

OTHER PUBLICATIONS

Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, a GE Healthcare Publication. Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Swiss; Medical Care., "CT Expres Contrast Media Delivery System Operation Manual Rev 1", 2004.
"The Solution for Your IV Formulas", Valley Lab. Inc., E-39-15, 3399, 3400, 2646.
Ulrich; Medical., "Instructions for Use for ulrichINJECT CT motion—CT Contrast Media Injector", 2018.
Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.
Wada, D.R. and Ward, D.S., "Open loop control of multiple drug effects in anesthesia", IEEE Transactions on Biomedical Engineering, vol. 42, Issue 7, pp. 666-677, 1995.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
Awai Kazuo; et al, "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.
"International Preliminary Report on Patentability from PCT App. No. PCT/US2019/048249", Mar. 11, 2021.

\* cited by examiner

| Contrast concentration | Flow rate (ml/s) | Pulse interval (ms) | Pulse flow rate (0.1 ml/s) | Pulse volume (0.1 ml) |
|---|---|---|---|---|
| 95 | 1 | 50 | 3 | 4 |
| 95 | 2 | 50 | 6 | 4 |
| 95 | 3 | 50 | 10 | 4 |
| 95 | 4 | 50 | 12.5 | 4 |
| 95 | 5 | 50 | 17.5 | 4 |

# FLUID INJECTOR SYSTEM, METHOD OF PREVENTING FLUID BACKFLOW, AND COMPUTER PROGRAM PRODUCT

CROSS-REFERENCE TO RELATED APPLICATION

This application is a U.S. national phase application under 35 U.S.C. § 371 of PCT International Application No. PCT/US2019/048249, filed Aug. 27, 2019 and claims the benefit of U.S. Provisional Patent Application No. 62/723,739, filed Aug. 28, 2018, the disclosures of which are hereby incorporated by reference in their entirety.

BACKGROUND OF THE DISCLOSURE

Field of the Disclosure

The present disclosure is related to a fluid injector system and, particularly, to a fluid injector system configured to perform an injection protocol. The present disclosure is further directed to a method of preventing a second fluid from a second fluid reservoir from flowing back into a first fluid reservoir during a fluid injection procedure using a fluid injector system. The present disclosure is also directed to a computer program product for preventing at least a second fluid from a second fluid reservoir from flowing back into a first fluid reservoir during a fluid injection procedure using a fluid injector system.

Description of Related Art

In many medical diagnostic and therapeutic procedures, a medical practitioner, such as a physician or radiologist, injects a patient with one or more fluids. In recent years, a number of injector-actuated syringes and powered injectors for pressurized injection of fluids have been developed for use in procedures such as angiography, computed tomography (CT), molecular imaging (such as PET imaging), and magnetic resonance imaging (MRI). In these procedures, a fluid, such as a contrast agent, may be used to highlight certain internal organs or portions of the body during an imaging process. Meanwhile, saline, or a similar flushing agent, may be used to ensure complete injection of the bolus of the contrast agent or adjust the concentration of the contrast agent.

For fluid injector systems with multi-reservoir disposables set up to deliver more than one fluid type, prevention of unintended mixing of the two fluids in the different reservoirs is desired. It may be particularly relevant for multi-patient applications, where the same reservoir(s) may be used to deliver fluid to multiple patients over the in-use life of a disposable reservoir. Unintended mixing of contrast into the saline reservoir may result in error in patient dosing during test injections or flush phases. Conversely, unintended mixing of saline into the contrast reservoir can result in undesired diluted doses producing images that are non-diagnostic or of reduced quality. Accordingly, there is room for improvement in fluid injector systems, methods of preventing fluid backflow, and computer program products for use in the same.

SUMMARY OF THE DISCLOSURE

These needs and others are met by embodiments of the disclosed examples or aspects, which are directed to an improved fluid injector system, method of preventing fluid backflow, and computer program product for use in same.

In some examples or aspects of the present disclosure, a fluid injector system configured to perform an injection protocol is provided. The fluid injector system includes a control device operatively associated with each of two or more drive components configured to pressurize and inject a first fluid from a first fluid reservoir through a fluid conduit, and at least a second fluid from a second fluid reservoir through the fluid conduit, the fluid conduit being in selective fluid communication with the first fluid reservoir and at least the second fluid reservoir. The control device has at least one processor programmed or configured to actuate a second drive component of the two or more drive components to pressurize and inject the second fluid through the fluid conduit, and while the second drive component is actuated, actuate a first drive component of the two or more drive components to introduce intermittent pulses of the first fluid to create a flow front interface between the first fluid and the second fluid in the fluid conduit to prevent backflow of the second fluid through the fluid conduit into the first fluid reservoir.

In some examples or aspects of the present disclosure, another fluid injector system configured to perform an injection protocol is provided. The fluid injector system includes a control device operatively associated with each of two or more drive components configured to pressurize and inject a first fluid from a first fluid reservoir through a fluid conduit, and at least a second fluid from a second fluid reservoir through the fluid conduit, the fluid conduit being in selective fluid communication with the first fluid reservoir and at least the second fluid reservoir. The control device has at least one processor programmed or configured to actuate a second drive component of the two or more drive components to pressurize and inject the second fluid through the fluid conduit, while the second drive component is actuated, actuate a first drive component of the two or more drive components to introduce intermittent pulses of the first fluid to create a flow front interface between the first fluid and the second fluid in the fluid conduit to prevent backflow of the second fluid through the fluid conduit in to the first fluid reservoir, continue to introduce intermittent pulses of the first fluid until the pressure of the first fluid reaches a pressure that is substantially the same as a pressure of the second fluid, decrease the intermittent pulses of the first fluid and deliver the first fluid at a first fluid flow rate and the second fluid at a second fluid flow rate at a desired ratio of the first fluid and the second fluid through the fluid conduit, either monitor the pressure in the first fluid reservoir and the pressure in the second fluid reservoir during injection of the first fluid and the second fluid to determine if a difference between the pressure in the first fluid reservoir and the pressure in the second fluid reservoir reaches a first predetermined value, or monitor an injection pressure in the fluid conduit and determine whether the injection pressure changes by a second predetermined value, and once a corresponding one of the first predetermined value and the second predetermined value is reached, restart the intermittent pulses of the first fluid through the fluid conduit in order to prevent the second fluid from entering the first fluid reservoir.

In some examples or aspects of the present disclosure, a method of preventing a second fluid from a second fluid reservoir from flowing back into a first fluid reservoir in a fluid injector system configured to perform an injection protocol is provided. The method includes providing a control device operatively associated with a first drive component and a second drive component, the first drive component configured to pressurize and inject the first fluid through patient fluid conduit, the second drive component configured to pressurize and inject at least a second fluid from the second fluid reservoir through the fluid conduit; actuating the second drive component of the two or more drive components to pressurize and inject the second fluid through the fluid conduit; and while the second drive component is actuated, actuating the first drive component of the two or more drive components to introduce intermittent pulses of the first fluid to create a flow front interface between the first fluid and the second fluid in the fluid conduit to prevent backflow of the second fluid through the fluid conduit into the first fluid reservoir.

In some examples or aspects of the present disclosure, a computer program product for preventing at least a second fluid from a second fluid reservoir from flowing back into a first fluid reservoir using a fluid injector system configured to perform an injection protocol is provided. The fluid injector system includes a control device operatively associated with each of a first drive component configured to pressurize and inject a first fluid through a fluid conduit, and at least a second drive component configured to pressurize and inject the second fluid through the fluid conduit, the fluid conduit being in selective fluid communication with the first fluid reservoir and the second fluid reservoir. The computer program product has non-transitory computer readable media including one or more instructions that, when executed by at least one processor, cause the at least one processor to actuate the second drive component to pressurize and inject the second fluid through the fluid conduit, and while the second drive component is actuated, actuate the first drive component to introduce intermittent pulses of the first fluid to create a flow front interface between the first fluid and the second fluid in the fluid conduit to prevent backflow of the second fluid through the fluid conduit into the first fluid reservoir.

Various other aspects of the present disclosure are recited in one or more of the following clauses:

Clause 1. A fluid injector system configured to perform an injection protocol, the fluid injector system comprising: a control device operatively associated with each of two or more drive components configured to pressurize and inject a first fluid from a first fluid reservoir through a fluid conduit, and at least a second fluid from a second fluid reservoir through the fluid conduit, the fluid conduit being in selective fluid communication with the first fluid reservoir and at least the second fluid reservoir, the control device comprising at least one processor programmed or configured to: actuate a second drive component of the two or more drive components to pressurize and inject the second fluid through the fluid conduit; and while the second drive component is actuated, actuate a first drive component of the two or more drive components to introduce intermittent pulses of the first fluid to create a flow front interface between the first fluid and the second fluid in the fluid conduit to prevent backflow of the second fluid through the fluid conduit into the first fluid reservoir.

Clause 2. The fluid injector system of clause 1, wherein the at least one processor is further programmed or configured to actuate the first drive component of the two or more drive components to continue to introduce intermittent pulses of the first fluid until a pressure of the first fluid reaches a pressure substantially the same as a pressure of the second fluid.

Clause 3. The fluid injector system of clause 1 or 2, wherein the at least one processor is further programmed or configured to further actuate the first drive component of the two or more drive components to introduce intermittent pulses of the first fluid at a frequency or amplitude selected from the group consisting of an increasing frequency, a decreasing frequency, an increasing amplitude, a decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and second fluid, a change in a fluid flow rate or pressure in the fluid conduit, a detection of backflow of the second fluid, a difference in fluid properties of the first fluid and second fluid, and combinations of any thereof.

Clause 4. The fluid injector system of any of clauses 1 to 3, wherein the at least one processor is further programmed or configured to decrease at least one of a frequency and an amplitude of or alter a wave form of the intermittent pulses of the first fluid and deliver the first fluid at a first fluid flow rate and the second fluid at a second fluid flow rate at a desired ratio of the first fluid and the second fluid through the fluid conduit.

Clause 5. The fluid injector system of any of clauses 1 to 4, wherein the at least one processor is further programmed or configured to monitor at least one of a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value.

Clause 6. The fluid injector system of clause 5, wherein, once the first predetermined value is reached, the at least one processor is further programmed or configured to start a second set of intermittent pulses of the first fluid through the fluid conduit in order to prevent the second fluid from entering the first fluid reservoir.

Clause 7. The fluid injector system of any of clauses 1 to 4, wherein the at least one processor is further programmed or configured to monitor an injection pressure in the fluid conduit and determine whether the injection pressure changes by a second predetermined value.

Clause 8. The fluid injector system of any of clauses 1 to 4, wherein the at least one processor is further programmed or configured to calculate a predetermined injection pressure based on at least one of a programmed injection protocol and user input information, and in response, adjust a pre-set waveform of the intermittent pulses.

Clause 9. The fluid injector system of any of clauses 1 to 8, wherein the at least one processor is further programmed or configured to continuously monitor a rate of change of an injection pressure in the fluid conduit, and in response, adjust at least one of a pulse interval, a pulse flow rate, and a pulse volume of the intermittent pulses based on a lookup table or a predetermined algorithm.

Clause 10. The fluid injector system of any of clauses 1 to 9, wherein, when the intermittent pulses of the first fluid are introduced, the at least one processor is further programmed or configured to select a pulse interval from a lookup table or a predetermined algorithm.

Clause 11. The fluid injector system of clause 10, wherein, when the intermittent pulses of the first fluid are introduced, the at least one processor is further programmed or configured to select a pulse flow rate from a lookup table or a predetermined algorithm.

Clause 12. The fluid injector system of any of clauses 1 to 11, wherein, when the intermittent pulses of the first fluid are introduced, the at least one processor is further programmed or configured to select a pulse volume from a lookup table or a predetermined algorithm.

Clause 13. The fluid injector system of any of clauses 10 to 12, wherein at least one of the lookup table and the predetermined algorithm is stored in a memory device.

Clause 14. The fluid injector system of any of clauses 1 to 13, wherein less than 40 milliliters of the first fluid are introduced into the fluid conduit before a pressure of the first fluid reaches a pressure that is substantially the same as a pressure of the second fluid.

Clause 15. The fluid injector system of clause 14, wherein less than 25 milliliters of the first fluid are introduced into the fluid conduit before a pressure of the first fluid reaches a pressure that is substantially the same as a pressure of the second fluid.

Clause 16. The fluid injector system of any of clauses 1 to 15, wherein, while the first drive component introduces intermittent pulses of the first fluid to create the flow front interface between the first fluid and the second fluid in the fluid conduit, a total volume of the first fluid introduced into the fluid conduit is less than the sum of a user programmed volume and 15 milliliters.

Clause 17. The fluid injector system of any of clauses 1 of 16, wherein, when the first drive component is actuated, a capacitance volume of the first fluid reservoir increases and none of the second fluid enters the first fluid reservoir.

Clause 18. A fluid injector system configured to perform an injection protocol, the fluid injector system comprising: a control device operatively associated with each of two or more drive components configured to pressurize and inject a first fluid from a first fluid reservoir through a fluid conduit, and at least a second fluid from a second fluid reservoir through the fluid conduit, the fluid conduit being in selective fluid communication with the first fluid reservoir and at least the second fluid reservoir, the control device comprising at least one processor programmed or configured to: actuate a second drive component of the two or more drive components to pressurize and inject the second fluid through the fluid conduit; while the second drive component is actuated, actuate a first drive component of the two or more drive components to introduce intermittent pulses of the first fluid to create a flow front interface between the first fluid and the second fluid in the fluid conduit to prevent backflow of the second fluid through the fluid conduit in to the first fluid reservoir; continue to introduce intermittent pulses of the first fluid until a pressure of the first fluid reaches a pressure that is substantially the same as a pressure of the second fluid; decrease at least one of a frequency and an amplitude of or alter a wave form of the intermittent pulses of the first fluid and deliver the first fluid at a first fluid flow rate and the second fluid at a second fluid flow rate at a desired ratio of the first fluid and the second fluid through the fluid conduit; either monitor at least one of a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value, or monitor an injection pressure in the fluid conduit and determine whether the injection pressure changes by a second predetermined value; and once a corresponding one of the first predetermined value and the second predetermined value is reached, start a second set of intermittent pulses of the first fluid through the fluid conduit in order to prevent the second fluid from entering the first fluid reservoir.

Clause 19. The fluid injector system of clause 18, wherein the at least one processor is further programmed or configured to further actuate the first drive component of the two or more drive components to introduce intermittent pulses of the first fluid at a frequency or amplitude selected from the group consisting of an increasing frequency, a decreasing frequency, an increasing amplitude, a decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and the second fluid, a change in a fluid flow rate or pressure in the fluid conduit, a detection of backflow of the second fluid, a difference in fluid properties of the first fluid and the second fluid, and combinations of any thereof.

Clause 20. The fluid injector system of clause 18 or 19, wherein the at least one processor is further programmed or configured to calculate a predetermined injection pressure based on at least one of a programmed injection protocol and user input information, and in response, adjust a pre-set waveform of the intermittent pulses.

Clause 21. The fluid injector system of any of clauses 18 to 20, wherein the at least one processor is further programmed or configured to continuously monitor a rate of change of an injection pressure in the fluid conduit, and in response, adjust at least one of a pulse interval, a pulse flow rate, and a pulse volume of the intermittent pulses based on a lookup table or a predetermined algorithm.

Clause 22. The fluid injector system of any of clauses 18 to 21, wherein, when the intermittent pulses of the first fluid are introduced, the at least one processor is further programmed or configured to select a pulse interval from a lookup table or predetermined algorithm.

Clause 23. The fluid injector system of clause 22, wherein, when the intermittent pulses of the first fluid are introduced, the at least one processor is further programmed or configured to select a pulse flow rate from a lookup table or a predetermined algorithm.

Clause 24. The fluid injector system of any of clauses 18 to 23, wherein, when the intermittent pulses of the first fluid are introduced, the at least one processor is further programmed or configured to select a pulse volume from a lookup table or predetermined algorithm.

Clause 25. The fluid injector system of any of clauses 22 to 24, wherein at least one of the lookup table and the predetermined algorithm is stored in a memory device.

Clause 26. The fluid injector system of any of clauses 18 to 25, wherein less than 40 milliliters of the first fluid are introduced into the fluid conduit before a pressure of the first fluid reaches a pressure that is substantially the same as a pressure of the second fluid.

Clause 27. The fluid injector system of clause 26, wherein less than 25 milliliters of the first fluid are introduced into the fluid conduit before a pressure of the first fluid reaches a pressure that is substantially the same as a pressure of the second fluid.

Clause 28. The fluid injector system of any of clauses 18 to 27, wherein, while the first drive component introduces intermittent pulses of the first fluid to create the flow front interface between the first fluid and the second fluid in the fluid conduit, a total volume of the first fluid introduced into the fluid conduit is less than the sum of a user programmed volume and 15 milliliters.

Clause 29. The fluid injector system of any of clauses 18 to 28, wherein, when the first drive component is actuated, a capacitance volume of the first fluid reservoir increases and none of the second fluid enters the first fluid reservoir.

Clause 30. A method of preventing a second fluid from a second fluid reservoir from flowing back into a first fluid reservoir in a fluid injector system configured to perform an injection protocol, the method comprising: providing a control device operatively associated with a first drive component and a second drive component, the first drive component configured to pressurize and inject the first fluid through patient fluid conduit, the second drive component configured to pressurize and inject at least a second fluid from the second fluid reservoir through the fluid conduit; actuating the second drive component of the two or more drive components to pressurize and inject the second fluid through the fluid conduit; and while the second drive component is actuated, actuating the first drive component of the two or more drive components to introduce intermittent pulses of the first fluid to create a flow front interface between the first fluid and the second fluid in the fluid conduit to prevent backflow of second fluid through the fluid conduit into first fluid reservoir.

Clause 31. The method of clause 30, further comprising programming or configuring the at least one processor to actuate the first drive component of the two or more drive components to continue to introduce intermittent pulses of the first fluid until a pressure of the first fluid reaches a pressure substantially the same as a pressure of the second fluid.

Clause 32. The method of clause 30 or 31, further comprising programming or configuring the at least one processor to further actuate the first drive component of the two or more drive components to introduce intermittent pulses of the first fluid at a frequency or amplitude selected from the group consisting of an increasing frequency, a decreasing frequency, an increasing amplitude, a decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and the second fluid, a change in a fluid flow rate or pressure in the fluid conduit, a detection of backflow of the second fluid, a difference in fluid properties of the first fluid and the second fluid, and combinations of any thereof.

Clause 33. The method of any of clauses 30 to 32, further comprising programming or configuring the at least one processor to decrease at least one of a frequency and an amplitude of or alter a wave form of the intermittent pulses of the first fluid and deliver the first fluid at a first fluid flow rate and the second fluid at a second fluid flow rate at a desired ratio of the first fluid and the second fluid through the fluid conduit.

Clause 34. The method of any of clauses 30 to 33, further comprising programming or configuring the at least one processor to monitor at least one of a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value.

Clause 35. The method of clause 34, further comprising, once the first predetermined value is reached, starting a second set of intermittent pulses of the first fluid through the fluid conduit with the at least one processor in order to prevent the second fluid from entering the first fluid reservoir.

Clause 36. The method of any of clauses 30 to 33, further comprising programming or configuring the at least one processor to monitor an injection pressure in the fluid conduit and determine whether the injection pressure changes by a second predetermined value.

Clause 37. The method of any of clauses 30 to 33, further comprising programming or configuring the at least one processor to calculate a predetermined injection pressure based on at least one of a programmed injection protocol and user input information, and in response, adjusting a pre-set waveform of the intermittent pulses.

Clause 38. The method of any of clauses 30 to 37, further comprising programming or configuring the at least one processor to continuously monitor a rate of change of an injection pressure in the fluid conduit, and in response, adjusting at least one of a pulse interval, a pulse flow rate, and a pulse volume of the intermittent pulses based on a lookup table or a predetermined algorithm.

Clause 39. The method of any of clauses 30 to 38, further comprising, when the intermittent pulses of the first fluid are introduced, selecting a pulse interval from a lookup table or a predetermined algorithm with the at least one processor.

Clause 40. The method of clause 39, further comprising, when the intermittent pulses of the first fluid are introduced, selecting a pulse flow rate from a lookup table or a predetermined algorithm with the at least one processor.

Clause 41. The method of any of clauses 30 to 40, further comprising, when the intermittent pulses of the first fluid are introduced, selecting a pulse volume from a lookup table or a predetermined algorithm with the at least one processor.

Clause 42. The method according to any of clauses 39-41, wherein at least one of the lookup table and the predetermined algorithm is stored in a memory device.

Clause 43. The method of any of clauses 30 to 42, wherein less than 40 milliliters of the first fluid are introduced into the fluid conduit before a pressure of the first fluid reaches a pressure that is substantially the same as a pressure of the second fluid.

Clause 44. The method of clause 43, wherein less than 25 milliliters of the first fluid are introduced into the fluid conduit before a pressure of the first fluid reaches a pressure that is substantially the same as a pressure of the second fluid.

Clause 45. The method of any of clauses 30 to 44, wherein, while the first drive component introduces intermittent pulses of the first fluid to create the flow front interface between the first fluid and the second fluid in the fluid conduit, a total volume of the first fluid introduced into the fluid conduit is less than the sum of a user programmed volume and 15 milliliters.

Clause 46. The method of any of clauses 30 to 45, wherein, when the first drive component is actuated, a capacitance volume of the first fluid reservoir increases and none of the second fluid enters the first fluid reservoir.

Clause 47. A computer program product for preventing at least a second fluid from a second fluid reservoir from flowing back into a first fluid reservoir using a fluid injector system configured to perform an injection protocol, the fluid injector system comprising a control device operatively associated with each of a first drive component configured to pressurize and inject a first fluid through a fluid conduit, and at least a second drive component configured to pressurize and inject the second fluid through the fluid conduit, the fluid conduit being in selective fluid communication with the first fluid reservoir and the second fluid reservoir, wherein the computer program product comprises non-transitory computer readable media comprising one or more instructions that, when executed by at least one processor, cause the at least one processor to: actuate the second drive component to pressurize and inject the second fluid through the fluid conduit; and while the second drive component is actuated, actuate the first drive component to introduce intermittent pulses of the first fluid to create a flow front interface between the first fluid and the second fluid in the fluid conduit to prevent backflow of the second fluid through the fluid conduit into the first fluid reservoir.

Clause 48. The computer program product of clause 47, wherein the at least one processor is further caused to actuate the first drive component to continue to introduce intermittent pulses of the first fluid until a pressure of the first fluid reaches a pressure that is substantially the same as a pressure of the second fluid.

Clause 49. The computer program product of clause 47 or 48, wherein the at least one processor is further caused to further actuate the first drive component of the two or more drive components to introduce intermittent pulses of the first fluid at a frequency or amplitude selected from the group consisting of an increasing frequency, a decreasing frequency, an increasing amplitude, a decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and the second fluid, a change in a fluid flow rate or pressure in the fluid conduit, a detection of backflow of the second fluid, a difference in fluid properties of the first fluid and the second fluid, and combinations of any thereof.

Clause 50. The computer program product of any of clauses 47 to 49, wherein the at least one processor is further caused to decrease at least one of a frequency and an amplitude of or alter a wave form of the intermittent pulses of the first fluid and deliver the first fluid at a first fluid flow rate and the second fluid at a second fluid flow rate at a desired ratio of the first fluid and the second fluid through the fluid conduit.

Clause 51. The computer program product of any of clauses 47 to 50, wherein the at least one processor is further caused to monitor at least one of a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value.

Clause 52. The computer program product of clause 51, wherein, once the first predetermined value is reached, the at least one processor is further caused to start a second set of intermittent pulses of the first fluid through the fluid conduit in order to prevent the second fluid from entering the first fluid reservoir.

Clause 53. The computer program product of any of clauses 47 to 50, wherein the at least one processor is further caused to monitor an injection pressure in the fluid conduit and determine whether the injection pressure changes by a second predetermined value.

Clause 54. The computer program product of any of clauses 47 to 50, wherein the at least one processor is further programmed or configured to calculate a predetermined injection pressure based on at least one of a programmed injection protocol and user input information, and in response, adjust a pre-set waveform of the intermittent pulses.

Clause 55. The computer program product of any of clauses 47 to 54, wherein the at least one processor is further caused to continuously monitor a rate of change of an injection pressure in the fluid conduit, and in response, adjust at least one of a pulse interval, a pulse flow rate, and a pulse volume of the intermittent pulses based on a lookup table or a predetermined algorithm.

Clause 56. The computer program product of any of clauses 47 to 55, wherein, when the intermittent pulses of the first fluid are introduced, the at least one processor is further caused to select a pulse interval from a lookup table or a predetermined algorithm.

Clause 57. The computer program product of clause 56, wherein, when the intermittent pulses of the first fluid are introduced, the at least one processor is further caused to select a pulse flow rate from a lookup table or a predetermined algorithm.

Clause 58. The computer program product of any of clauses 47 to 57, wherein, when the intermittent pulses of the first fluid are introduced, the at least one processor is further caused to select a pulse volume from a lookup table or a predetermined algorithm.

Clause 59. The computer program product of any of clauses 56 to 58, wherein at least one of the lookup table and the predetermined algorithm is stored in a memory device.

Clause 60. The computer program product of any of clauses 47 to 59, wherein less than 40 milliliters of the first fluid are introduced into the fluid conduit before a pressure of the first fluid reaches a pressure substantially the same as a pressure of the second fluid.

Clause 61. The computer program product of clause 60, wherein less than 25 milliliters of the first fluid are introduced into the fluid conduit before a pressure of the first fluid reaches a pressure that is substantially the same as a pressure of the second fluid.

Clause 62. The computer program product of any of clauses 47 to 61, wherein, while the first drive component introduces intermittent pulses of the first fluid to create the flow front interface between the first fluid and the second fluid in the fluid conduit, a total volume of the first fluid introduced into the fluid conduit is less than the sum of a user programmed volume and 15 milliliters.

Clause 63. The computer program product of any of clauses 47 to 62, wherein, when the first drive component is actuated, a capacitance volume of the first fluid reservoir increases and none of the second fluid enters the first fluid reservoir.

Further details and advantages of the various examples described in detail herein will become clear upon reviewing the following detailed description of the various examples in conjunction with the accompanying drawing figures.

DETAILED DESCRIPTION OF THE DISCLOSURE

Figure 1:
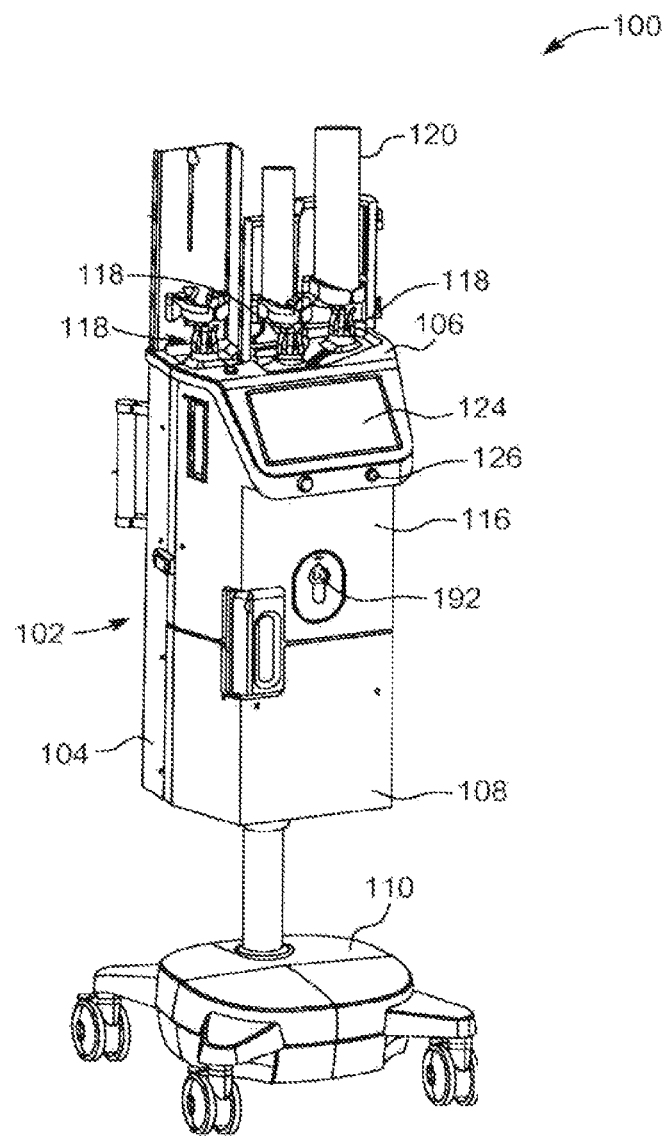
FIG. 1 is a perspective view of a multi-fluid delivery system, according to one example of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston for delivering fluid from a syringe.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a fluid reservoir, such as a syringe, a rolling diaphragm, or multiple syringe disposable set, the term "distal" refers to a portion of the fluid reservoir nearest to a patient. When used in relation to a fluid reservoir, such as a syringe, a rolling diaphragm, or multiple syringe disposable set, the term "proximal" refers to a portion of the fluid reservoir nearest to the injector system.

The term "open", when used to refer to a fluid delivery component, means that the fluid reservoir is in fluid connection with an outlet to atmospheric pressure or connected to a patient's vascular system, for example through a nozzle or the open end of a tubing component or catheter. In an open system, fluid flow may be constrained or restricted, for example by forcing a fluid through a small diameter fluid path where flow may be determined by physical parameters of the system and the fluid, such as tubing diameter, fluid path constrictions, applied pressure, viscosity, etc. The term "closed" or "closeable", when used to refer to a fluid delivery component, means that the fluid reservoir has at least one state in which the component is not in fluid connection with an outlet under atmospheric pressure or connected to a patient's vascular system or the fluid in the fluid reservoir is fluidly isolated, for example where fluid flow is stopped by a valve, such as a stopcock, high crack pressure valve, pinch valve, and the like, that closes a fluid pathway.

Referring to the drawings in which like reference characters refer to like parts throughout the several views thereof, one embodiment of the present disclosure is generally directed to a multi-fluid medical injector/injector system 100 (hereinafter "fluid injector system 100") which in certain embodiments may include a multi-patient disposable set (MUDS) 130 configured for delivering fluid to a patient using a single-use disposable set (SUDS) 190 connector and in other embodiments may include two or more disposable fluid reservoirs or syringes, which may be disposed after one injection procedure or a specific number of injection procedures. The fluid injector system 100 may include multiple components as individually described herein. Generally, the fluid injector system 100 depicted in FIGS. 1-3 has a powered injector or other administration device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein. While the various embodiments of the methods and processor are shown with reference to an injector system having a multi-use disposable set ("MUDS") and a single-use disposable set ("SUDS") configuration in FIGS. 1-3, the disclosure is not limited to such an injector system and may be utilized in other syringe based injector systems, such as but not limited to those described in U.S. Pat. Nos. 7,553,294, 7,563,249, 8,945,051, 9,173,995, 10,124,110; and U.S. application Ser. Nos. 15/305,285, 15/541,573, 15/568,505; the disclosures of each of which are incorporated herein in their entirety by this reference.

With reference to FIG. 1, a fluid injector system 100 according to one embodiment includes an injector housing 102 having opposed lateral sides 104, a distal or upper end 106, and a proximal or lower end 108. The housing 102 encloses the various mechanical drive components, electrical and power components necessary to drive the mechanical drive components, and control components, such as electronic memory and electronic control devices (hereinafter electronic control device(s)), used to control operation of reciprocally movable pistons 103 (not shown) associated with the fluid injector system 100 described herein. Such pistons 103 may be reciprocally operable via electro-mechanical drive components such as a ball screw shaft driven by a motor, a voice coil actuator, a rack-and-pinion gear drive, a linear motor, and the like. In some examples, at least some of the mechanical drive components, electrical and power components, and control components may be provided on the base 110.

With continued reference to FIG. 1, the fluid injector system 100 may have at least one door 116 that encloses at least a portion of the MUDS, the mechanical drive components, electrical and power components, and control components.

The fluid injector system 100 may include at least one bulk fluid connector 118 for connection with at least one bulk fluid source 120. In some examples, a plurality of bulk fluid connectors 118 may be provided. For example, as shown in the fluid injector embodiment illustrated in FIG. 1, three bulk fluid connectors 118 may be provided in a side-by-side or other arrangement. In some examples, the at least one bulk fluid connector 118 may include a spike configured for removably connecting to the at least one bulk fluid source 120, such as a vial, a bottle, or a bag. The at least one bulk fluid connector 118 may be formed on the multi-use disposable set ("MUDS), as described herein. The at least one bulk fluid source 120 may be configured for receiving a medical fluid, such as saline, an imaging contrast agent, or other medical fluid, for delivery to the patient by fluid injector system 100.

With continued reference to FIG. 1, embodiments of the fluid injector system 100 may include one or more user interfaces 124, such as a graphical user interface (GUI) display window. The user interface 124 may display information pertinent to a fluid injection procedure involving fluid injector system 100, such as patient information, the programmed injection protocol, injection status or progress, current flow rate, fluid pressure, and volume remaining in the at least one bulk fluid source 120 connected to the fluid injector system 100 and may be a touch screen GUI that allows an operator to input commands and/or data for operation of fluid injector system 100 as well as receiving operator commands from a remote input station or display. While the user interface 124 is shown on the injector housing 102, such user interface 124 may also be in the form of, or the fluid injector system 100 may additionally have, a remote display that is wired or wirelessly linked to the housing 102 and control and mechanical elements of fluid injector system 100, for example in a remote room designed to shield the user from exposure to x-rays. In some examples, the user interface 124 may be a tablet computer that is detachably connected to the housing 102 and is in wired or wirelessly linked communication with the housing 102. Additionally, the fluid injector system 100 and/or user interface 124 may include at least one control button 126 for tactile operation by an attendant operator of the fluid injector system 100. In certain examples, the at least one control button 126 may be part of a keyboard for inputting commands and/or data by the operator. The at least one control button 126 may be hard-wired to the electronic control device(s) associated with the fluid injector system 100 to provide direct input to the electronic control device(s). The at least one control button 126 may also be a graphical part of the user interface 124, such as a touch screen. In either arrangement, the at least one control button 126 desirably provides certain individual control features to the attendant operator of the fluid injector system 100, such as, but not limited to: (1) acknowledging that a multi-patient disposable set has been loaded or unloaded; (2) selecting or programing an injection protocol; (3) filling/purging of the fluid injector system 100; (4) inputting information and/or data related to the patient and/or injection procedure; (5) preloading the fluid injector system 100; and (6) initiating/stopping an injection procedure. The user interface 124 and/or any electronic processing units associated with the fluid injector system 100 may be wired or wirelessly connected to an operation and/or data storage system such as a hospital network system.

Figure 2:
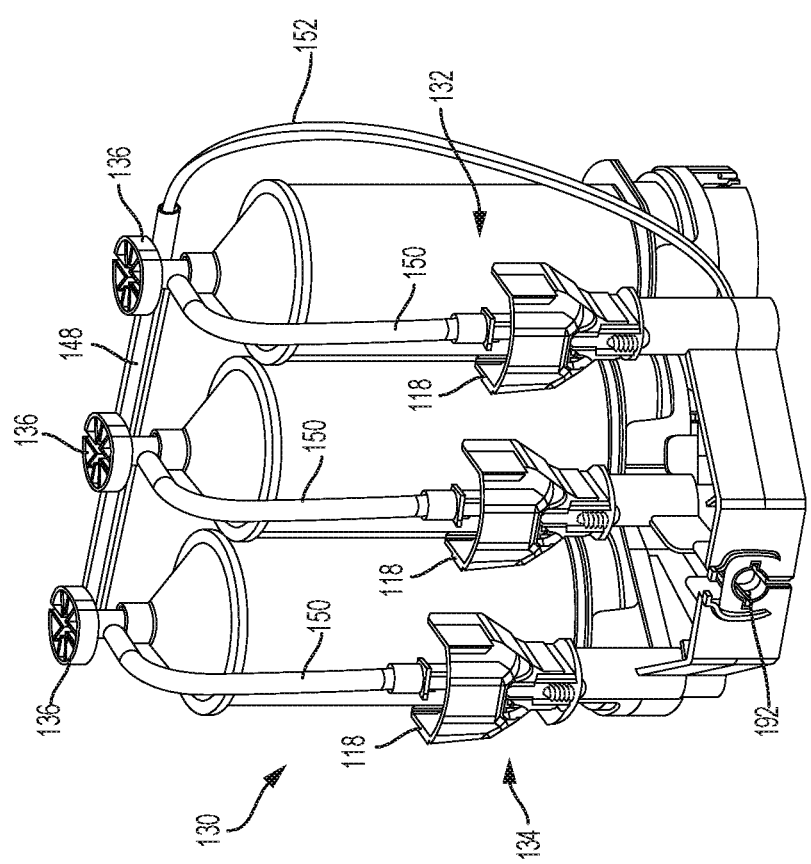
FIG. 2 is a perspective view of the multi-patient disposable set (MUDS) for use with the multi-fluid delivery system of FIG. 1.

With reference to FIG. 2, the embodiment of the fluid injector system 100 illustrated in FIG. 1 may include a MUDS 130 that is removably connected to the fluid injector system 100 for delivering one or more fluids from the one or more bulk fluid sources 120 to the patient. Examples and features of embodiments of the MUDS are further described in PCT International Publication No. WO 2016/112163, filed on Jan. 7, 2016, the disclosure of which is incorporated herein by reference in its entirety. The MUDS 130 may include one or more fluid reservoirs 132, such as one or more syringes. As used herein, the term "fluid reservoir" means any container capable of taking in and delivering a fluid, for example during a fluid injection procedure including, for example a syringe, a rolling diaphragm, a pump, a compressible bag, and the like. Fluid reservoirs may include the interior volume of at least a portion of a fluid pathway, such as one or more tubing lengths, that are in fluid communication with the interior of the fluid reservoir, including fluid pathway portions that remain in fluid communication with the fluid reservoir after the system is closed or fluidly isolated from the remainder of the fluid pathway. In some examples, the number of fluid reservoirs 132 may correspond to the number of bulk fluid sources 120. For example, with reference to FIG. 2, the MUDS 130 has three syringes 132 in a side-by-side arrangement such that each syringe 132 is fluidly connectable to one or more of the corresponding three bulk fluid sources 120. In some examples, one or more bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118 and a fluid inlet line 150. In some examples, the bulk fluid connector 118 may be provided directly on the MUDS 130.

With further reference to FIG. 2, the MUDS 130 is removably connectable to the housing 102 of the fluid injector system 100. As will be appreciated by one having ordinary skill in the art, it may be desirable to construct at least a portion of the MUDS 130 from a clear medical grade plastic in order to facilitate visual verification that a fluid connection has been established with the fluid injector system 100 or that air has been removed from the fluid reservoir. Visual verification is also desirable for confirming that air bubbles are generally not present within various fluid connections, for example after performing an air removal protocol, such as described herein. Various optical sensors (not shown) may also be provided to detect air either in the fluid lines or the fluid reservoir during a priming operation.

With continued reference to FIG. 2, the MUDS 130 may include one or more valves 136, such as stopcock valves, for controlling which medical fluid or combinations of medical fluids are withdrawn from the multi-dose bulk fluid source 120 (see FIG. 1) into the fluid reservoirs 132 and/or are delivered to a patient from each fluid reservoir 132. In some examples, the one or more valves 136 may be provided on a distal end of the plurality of syringes 132 or on a manifold 148. The manifold 148 may be in selectable fluid communication via valves 136 with the interior volume of the syringes 132. The interior volume of the syringes 132 may be in selectable fluid communication via valves 136 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the interior volume of the one or more syringes 132 or it may be delivered from the interior volume of the one or more syringes 132. In a first position, such as during the filling of the syringes 132, the one or more valves 136 are oriented such that fluid flows from the bulk fluid source 120 into the desired syringe 132 through a fluid inlet line 150, such as a MUDS fluid path. During the filling procedure, the one or more valves 136 are positioned such that fluid flow through one or more fluid outlet lines 152 or manifold 148 is blocked or closed. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked or closed. In a third position, the one or more valves 136 are oriented such that fluid flow through the one or more fluid inlet lines 150 and the one or more fluid outlet lines 152 or manifold 148 is blocked or closed. Thus, in the third position, each of the one or more valves 136 isolates the corresponding syringe 132 and prevents fluid flow into and out of the interior volume of the corresponding syringe 132. As such, each of the one or more syringes 132 and the corresponding valve 136 defines a closed system.

The one or more valves 136, fluid inlet lines 150, and/or fluid outlet lines 152 may be integrated into or in fluid communication via the manifold 148. The one or more valves 136 may be selectively positioned to the first or second position by manual or automatic handling. For example, the operator may position the one or more valves 136 into the desired position for filling, fluid delivery, or the closed position. In other examples, at least a portion of the fluid injector system 100 is operable for automatically positioning the one or more valves 136 into a desired position for filling, fluid delivery, or the closed position based on input by the operator or by a protocol in the system controller.

Having generally described the components of the fluid injector system 100 and the MUDS 130, the structure and method of use of a single-use disposable set 190 (SUDS) and its interaction with MUDS 130 will now be described.

Figure 3:
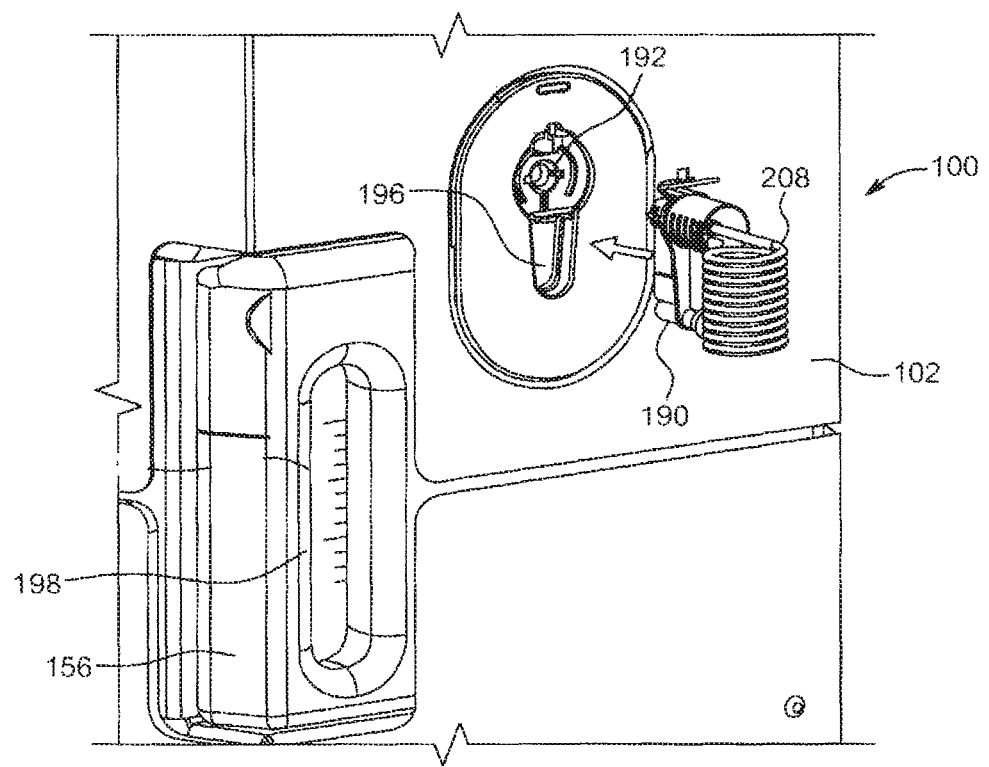
FIG. 3 is a perspective view of a connection interface prior to connecting a single-use disposable set (SUDS) connector with a multi-fluid delivery system.

With reference to FIG. 3, according to the described embodiment the fluid injector system 100 has a connection port 192 that is configured to form a releasable fluid connection with at least a portion of the SUDS 190. In some examples, the connection port 192 may be formed on the MUDS 130. As described herein, the SUDS 190 may be connected to the connection port 192, formed on at least a portion of the MUDS 130 and/or the housing 102. Desirably, the connection between the SUDS 190 and the connection port 192 is a releasable connection to allow the SUDS 190 to be selectively disconnected from the connection port 192 and connected to the connection port 192. In some examples, the SUDS 190 may be disconnected from the connection port 192 and disposed after each fluid delivery procedure, and a new SUDS 190 may be connected to the connection port 192 for a subsequent fluid delivery procedure. The SUDS 190 may be used to deliver one or more medical fluids to a patient by SUDS fluid line 208 having a distal end that may be selectively disconnected from the body of the SUDS 190 and connected to a patient catheter. Other examples and features of the SUDS 190 are described in U.S. Patent Publication No. 2016/0331951, filed Jul. 7, 2016, the disclosure of which is incorporated herein by reference.

Figure 4:
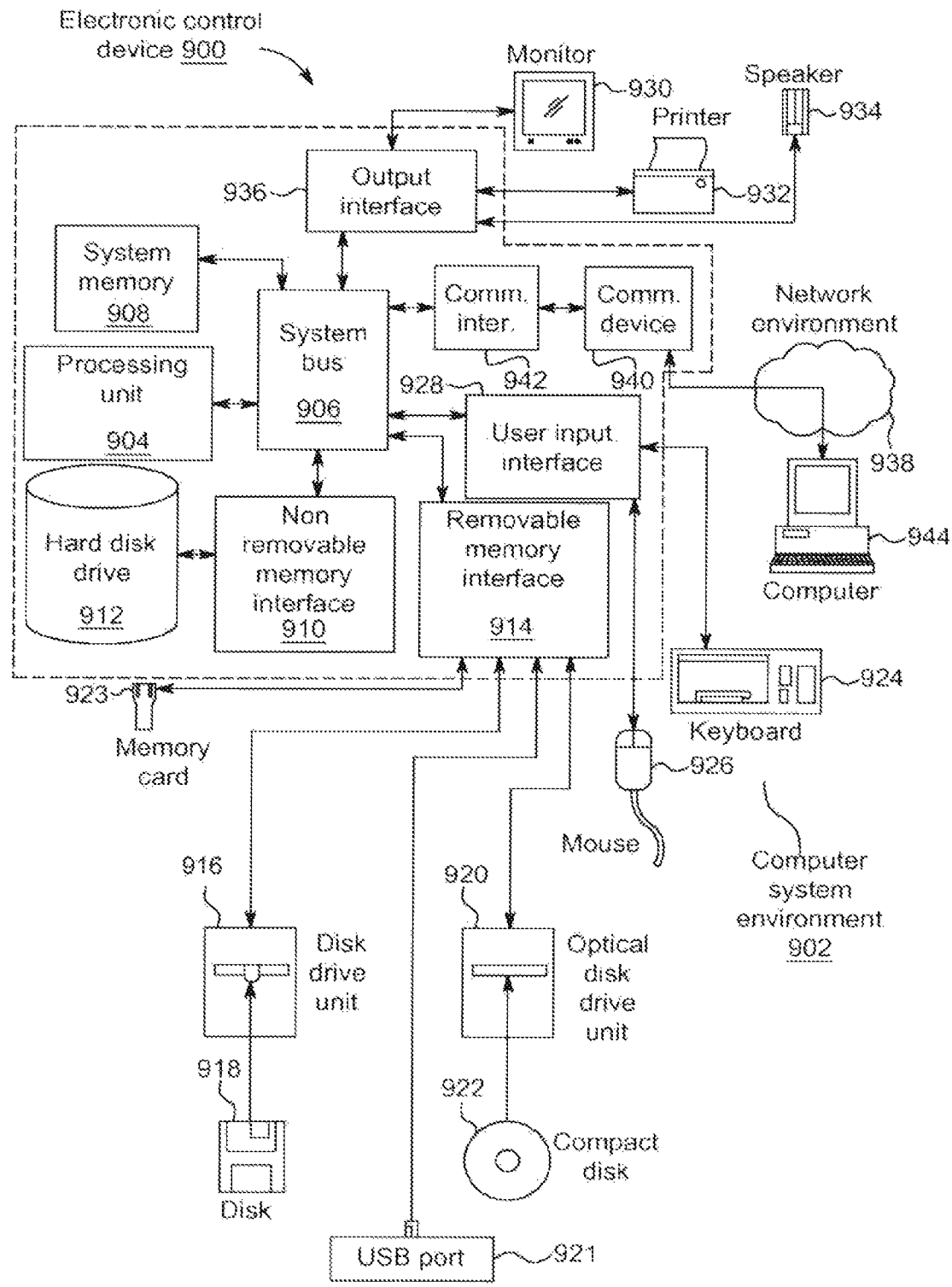
FIG. 4 is a schematic view of an electronic control system of a multi-fluid delivery system in accordance with some examples.

With reference to FIG. 4, an electronic control device 900 may be associated with fluid injector system 100 to control the filling and delivery operations of the fluid injector 100. In some examples, the electronic control device 900 may control the operation of various valves, stopcocks, piston members, and other elements to affect a desired gas/air removal, filling, and/or delivery procedure. For example, the electronic control device 900 may include a variety of discrete computer-readable media components. For example, this computer-readable media may include any media that can be accessed by the electronic control device 900, such as volatile media, non-volatile media, removable media, non-removable media, transitory media, non-transitory media, etc. As a further example, this computer-readable media may include computer storage media, such as media implemented in any method or technology for storage of information, such as computer-readable instructions, data structures, program modules, or other data; random access memory (RAM), read-only memory (ROM), electrically erasable programmable read-only memory (EEPROM), flash memory, cloud storage media, or other memory technology; solid state memory, cloud memory, CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic control device 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic control device 900 further includes a system memory 908 with computer storage media in the form of volatile and non-volatile memory, such as ROM and RAM. A basic input/output system (BIOS) with appropriate computer-based routines assists in transferring information between components within the electronic control device 900 and is normally stored in ROM. The RAM portion of the system memory 908 typically contains data and program modules that are immediately accessible to or presently being operated on by a processor 904, e.g., an operating system, application programming interfaces, application programs, program modules, program data, and other instruction-based computer-readable codes.

With continued reference to FIG. 4, the electronic control device 900 may also include other removable or non-removable, volatile or non-volatile, transitory or non-transitory computer storage media products. For example, the electronic control device 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in an exemplary computing system environment 902, including, but not limited to, magnetic tape cassettes and floppy disks, CDs, DVDs, digital video tape, solid state RAM, solid state ROM, cloud memory, etc. These various removable or non-removable, volatile or non-volatile magnetic media are in communication with the processor 904 and other components of the electronic control device 900 via a system bus 906. The drives and their associated computer storage media, discussed above and illustrated in FIG. 4, provide storage of operating systems, computer-readable instructions, application programs, data structures, program modules, program data, and other instruction-based, computer-readable code for the electronic control device 900 (whether duplicative or not of this information and data in the system memory 908).

A user may enter commands, information, and data into the electronic control device 900 through certain attachable or operable input devices, such as the user interface 124 shown in FIG. 1, via a user input interface 928. A variety of such input devices may be utilized, e.g., a microphone, a trackball, a joystick, a touchpad, a touch-screen, a scanner, etc., including any arrangement that facilitates the input of data and information to the electronic control device 900 from an outside source. As discussed, these and other input devices are often connected to the processor 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic control device 900 through an output interface 936 coupled to the system bus 906. It is envisioned that any such peripheral output devices be used to provide information and data to the user.

The electronic control device 900 may operate in a network environment 938 through the use of a communications device 940, which is integral to the electronic control device 900 or remote therefrom. This communications device 940 is operable by and in communication with the other components of the electronic control device 900 through a communications interface 942. Using such an arrangement, the electronic control device 900 may connect with or otherwise communicate with one or more remote computers, such as a remote computer 944, which may be a personal computer, a server, a router, a network personal computer, a peer device, or other common network nodes, and typically includes many or all of the components described above in connection with the electronic control device 900. Using appropriate communication devices 940, e.g., a modem, a network interface or adapter, etc., the computer 944 may operate within and communicate through a local area network (LAN) and a wide area network (WAN), but may also include other networks such as a virtual private network (VPN), an office network, a hospital network, an enterprise network, an intranet, the Internet, etc.

As used herein, the electronic control device 900 includes or is operable to execute appropriate custom-designed or conventional software to perform and implement the processing steps of the method and system of the present disclosure, thereby forming a specialized and particular computing system. Accordingly, the method and system may include one or more electronic control devices 900 or similar computing devices having a computer-readable storage medium capable of storing computer-readable program code or instructions that cause the processor 904 to execute, configure, or otherwise implement the methods, processes, and transformational data manipulations discussed hereinafter in connection with the present disclosure. Still further, the electronic control device 900 may be in the form of a personal computer, a personal digital assistant, a portable computer, a laptop, tablet, a palmtop, a mobile device, a mobile telephone, a server, or any other type of computing device having the necessary processing hardware and software to appropriately process data to effectively implement the computer-implemented method and system.

It will be apparent to one skilled in the relevant arts that the system may utilize databases, such as, for example look-up tables, physically located on or accessible by one or more computers which may or may not be the same as their respective servers. For example, programming software on electronic control device 900 can control a database physically stored on a separate processor of the network or otherwise.

In some examples, the electronic control device 900 may be programmed to measure and/or monitor one or more injection parameters during an injection protocol, such as an injection parameter selected from the group consisting of a pressure of a fluid in each of the various fluid reservoirs, a pressure in a fluid conduit downstream of the fluid reservoirs, a fluid flow rate of each fluid as it enters or exits each of the fluid reservoirs, a fluid flow rate of a fluid in the fluid conduit, a presence of a fluid backflow in the fluid conduit, a viscosity of a fluid in a fluid reservoir and/or in a fluid conduit, a temperature of a fluid in a fluid reservoir, a speed of a drive component, such as a piston or plunger for each of the various fluid reservoirs, a pulsing frequency and/or amplitude of a pulse sequence of a drive component, and various combinations thereof. The control device 900 may measure and/or the one or more injection parameters by being in electrical and/or mechanical communication with one or more sensors associated with the fluid injection system. Based on the measured and/or monitored injection parameters, the control device 900 may alter, adjust, initiate, or stop a corresponding operation, for example if a sensor reads that an injection parameter is outside a desired range or is trending towards going outside a desired range, so that the parameter is adjusted back towards or within the desired range.

Figure 5:
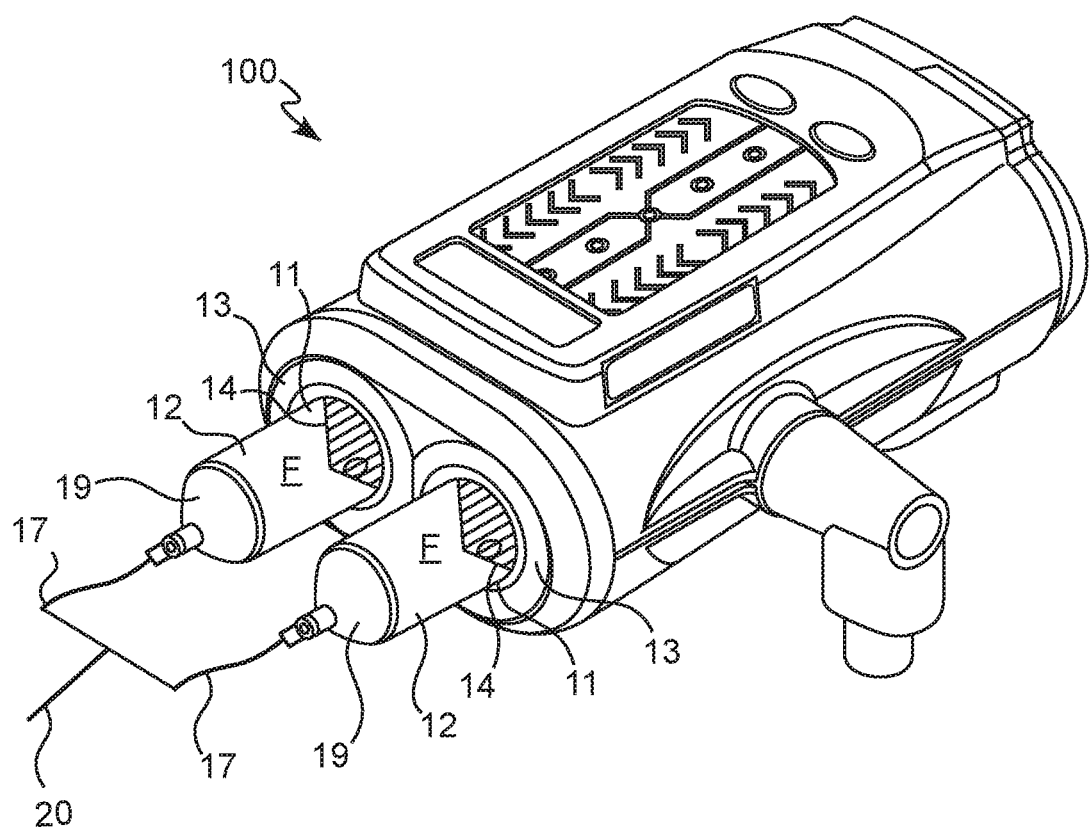
FIG. 5 is a perspective view of a multi-fluid delivery system, according to another example of the present disclosure.

While FIGS. 1-3 illustrate one example of a fluid injector system 100 and associated components and structure, it is to be understood that the present disclosure is not limited to any particular type or variety of the fluid injector system 100. Referring now to FIG. 5, another non-limiting example of a fluid injector system 100 in accordance with the present disclosure includes at least one fluid reservoir, such as syringe 12, at least one piston 103 (not shown) connectable to at least one plunger 14, and a fluid control module (not pictured, such as control device 900). The at least one syringe 12 is generally adapted to interface with at least one component of the system, such as a syringe port 13. The fluid injector system 100 is generally configured to deliver at least one fluid F to a patient during an injection procedure. The fluid injector system 100 is configured to releasably receive the at least one syringe 12, which is to be filled with at least one fluid F, such as a contrast media, saline solution, or any desired medical fluid. The system may be a multi-syringe injector, wherein several syringes may be oriented side-by-side or in another spatial relationship and are separately actuated by respective pistons associated with the injector. The at least one syringe 12 may be oriented in any manner such as upright, downright, or positioned at any degree angle. In another embodiment, a fluid injector 100 may interface with one or more rolling diaphragm syringes (not shown). Non-limiting examples of rolling diaphragm syringe based injectors are described in U.S. application Ser. Nos. 15/305,285, and 15/568,505 and PCT International Application No. PCT/US2017/056747, the disclosures of which are incorporated herein.

With continued reference to FIG. 5, the injector system 100 may be used during a medical procedure to inject the at least one medical fluid F into the vasculature system of a patient by driving a plunger 14 of at least one syringe 12 with a drive component, such as the at least one piston 103 (not shown). The at least one piston may be reciprocally operable upon at least a portion of the at least one syringe, such as the plunger 14. Upon engagement, the at least one piston may move the plunger 14 toward the distal end 19 of the at least one syringe, as well as retracting plunger 14 toward proximal end 11 of at least one syringe 12.

A tubing set (e.g., first and second fluid conduits 17a and 17b, and common fluid conduit 20) may be in fluid communication with an outlet port of each syringe 12 to place each syringe in fluid communication with a catheter for delivering the fluid F from each syringes 12 to the catheter (not shown) inserted into a patient at a vascular access site. The first and second fluid conduits 17a and 17b may be connected to the common fluid conduit 20 by any suitable mechanism known in the art (e.g., a Y-connector or a T-connector). In certain embodiments, fluid flow from the one or more syringes 12 may be regulated by a fluid control module, which may be the same or similar to the electronic control device 900, that operates various drive components, valves, stopcocks, and flow regulating structures to regulate the delivery of the at least one fluid to the patient based on user selected injection parameters, such as injection flow rate, fluid pressure within each syringe, fluid flow rate in a fluid conduit duration, and total injection volume. The fluid control module is generally configured to perform various functions, those of which have the ability to aid in the prevention of backflow of fluid from one syringe to the other syringe of the system, as will be described herein, along with other various embodiments.

In some examples, the fluid control module may instruct the fluid injector system 100 to fill the at least one syringe 12 with the at least one fluid F. The fluid injector system 100 may have a plurality of bulk fluid sources, for example a bulk contrast fluid source and a bulk saline source, one for each of the syringes 12, for filling each of the syringes with the desired fluid. Filling the at least one syringe 12 with the at least one fluid F may be done by placing the at least one syringe 12 in fluid communication with at least one bulk fluid source and instructing the fluid injector system 100 to retract the piston, being removably engaged with the plunger 14 of the at least one syringe 12, from the distal end 19 of the at least one syringe toward the proximal end 11 of the at least one syringe. In certain embodiments, the fluid injector system 100 and fluid control module may be programmed to perform an air removal protocol. As shown in FIG. 5, the fluid injector system 100 may be an open system, i.e., the two syringes 12 may be in fluid connection with the first and second fluid conduits 17a and 17b that connect to the common fluid conduit 20 without any intermediate valving or stopcocks. In such an open system, a difference in fluid pressure in a first syringe relative to the fluid pressure in a second syringe may result in backflow of fluid from the higher pressure syringe into the lower pressure syringe. Such a situation, for example where a higher pressure contrast fluid flows into the lower pressure saline syringe may result, for example, in inaccuracies in delivered fluid amounts, less than optimal images from an imaging procedure, and wasting of medical fluid. According to other embodiments, the fluid injector system 100 may be a closed system, for example where the distal end 19 of each of the syringes 12 and/or the first and second fluid conduits 17a and 17b may include one or more valves or stop cocks to fluidly isolate the interior of each syringe from the other of the first and second fluid conduits 17 and 17b, and the other syringe 12.

For injector systems with multi-reservoir disposables, such as a fluid injector system with two or more syringes as described and illustrated herein, that is set up to deliver more than one fluid type, such as a contrast fluid and a saline flushing fluid, prevention of unintended mixing of the two fluids in the different reservoirs is desired. It may be particularly relevant for multi-patient applications, where the same reservoir(s) may be used for multiple patients over the in-use life of a disposable reservoirs. Unintended mixing of, for example, contrast into a saline reservoir may result in unintended patient dosing during test injections or flush phases. Conversely, unintended mixing of saline into a contrast reservoir can result in diluted doses producing images that are non-diagnostic or of reduced quality.

For certain injectors, the orientation of the disposables may be fixed for the duration of use. For example, in some injectors the reservoirs are always oriented with the distal outlet of the reservoirs facing upwards. In such a reservoir setup, any fluid mixing that involves a denser fluid which enters from the top of the reservoir and continues downward into the occupying fluid. Given the relative density of contrast and saline, this means that if contrast were to enter the saline reservoir, it would sink to the bottom. Since the contrast would set at the bottom of the reservoir in a vertical setup, it would be the last fluid delivered from a reservoir. Repeated flow of contrast into the saline reservoir would continue to increase the contrast percentage in the saline reservoir with each injection. Saline mixing into the contrast reservoir would have the opposite effect. The lighter saline fluid remains trapped at the top of the contrast reservoir, with only a small portion dispersing into the occupying contrast depending on the velocity of the fluid at entry. As a result, saline would be injected out at the beginning of the next contrast phase, minimizing the effect of repeated mixing over time but resulting in an inaccurate dose of contrast being administered to a patient. According to other embodiments, such as the injector shown in FIG. 5, the fluid injector head may be swiveled so that the distal ends of the syringes point in a generally downward direction. In this embodiment, backflow of a more dense contrast into the saline syringe would result in contrast pooling at the distal tip of the syringe, such that when the fluid injector is programmed to inject saline, the contrast at the distal tip is injected first, resulting in over administration and waste of contrast and impacting the quality of the image obtained. Backflow of saline into the contrast syringe would result in pooling of the saline at the proximal end of the syringe near the plunger which would dilute the contrast dose administered when the contrast syringe has a low volume of fluid within it, impacting the quality of the image obtained.

The cause of mixing between the reservoirs is due to a phenomenon identified as backflow, wherein a higher pressure fluid moves upstream against a flow of a lower pressure fluid. Backflow is based, at least in part, on the physics of pressure gradients. The underlying principle is that flow occurs in the direction of decreasing pressure, e.g., flow propagates from a point of highest pressure to point of lowest pressure. In certain disposables, this pathway tends to travel from the injecting reservoir, down the patient tubing set, and out of the catheter. The reservoir is the point of highest pressure as pressure in the reservoir is generated by the displacement of the fluid by the drive component. The magnitude of the pressure depends on the fluid viscosity, flow rate, mechanical slack of injector components under load, expansion of the syringe and tubing material under fluid pressure, and downstream impedance (e.g., without limitation, ID of syringe outlet, catheter gauge and tube set ID). If two reservoirs are open simultaneously, the risk of backflow is present if the pressure is different between the two reservoirs. The reservoir with the lowest pressure will be susceptible to introduction of the higher pressure fluid via backflow through the connecting tubing set. Backflow via this mechanism may also occur or be exacerbated due to the compliant nature of the reservoirs, which expand in volume with increased pressure and load on mechanical components of the system. As previously stated, the risk of unintended mixing of fluids is only present when at least two of the three reservoirs are open to the patient line in the manifold.

Figure 6A:
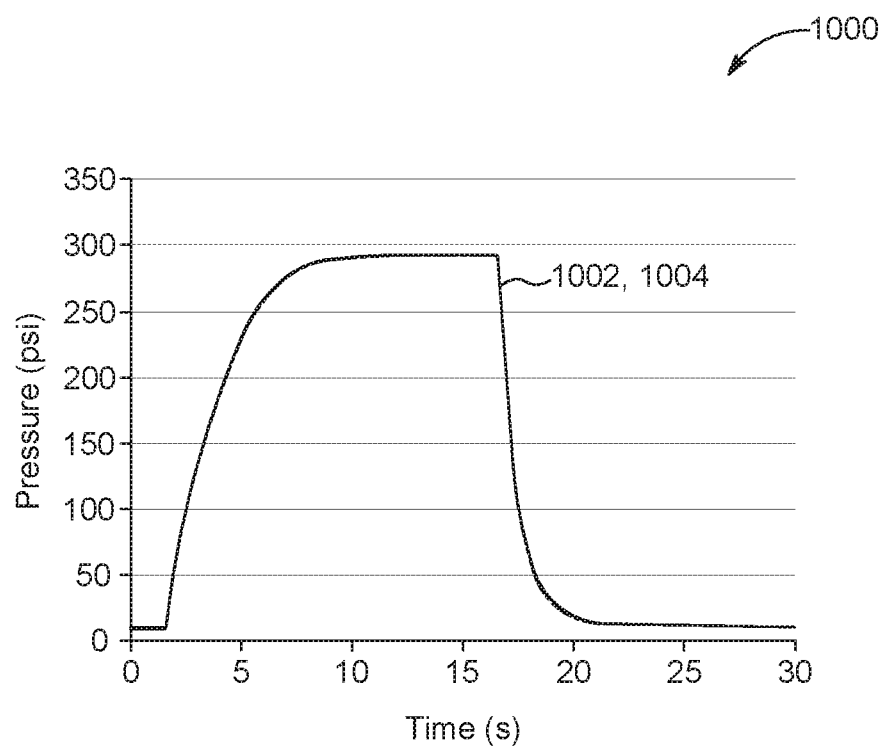
FIG. 6A is a graph showing pressure versus time of a first fluid and a second fluid, wherein the first and second fluids develop the same pressure over time.
Figure 6B:
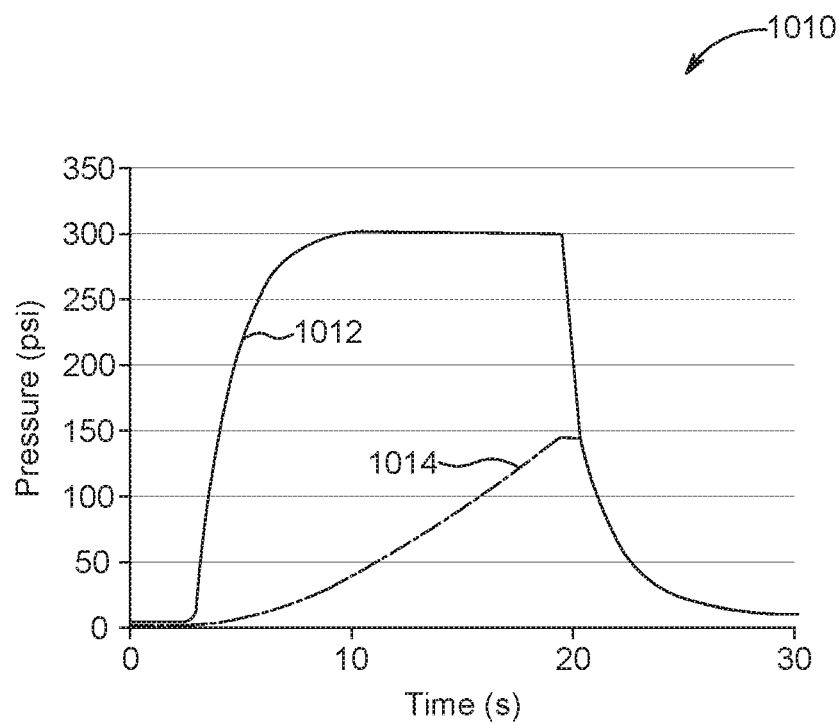
FIG. 6B is a graph showing pressure versus time of a first fluid and a second fluid, wherein the pressure of the first and second fluids differs over time.
Figure 7:
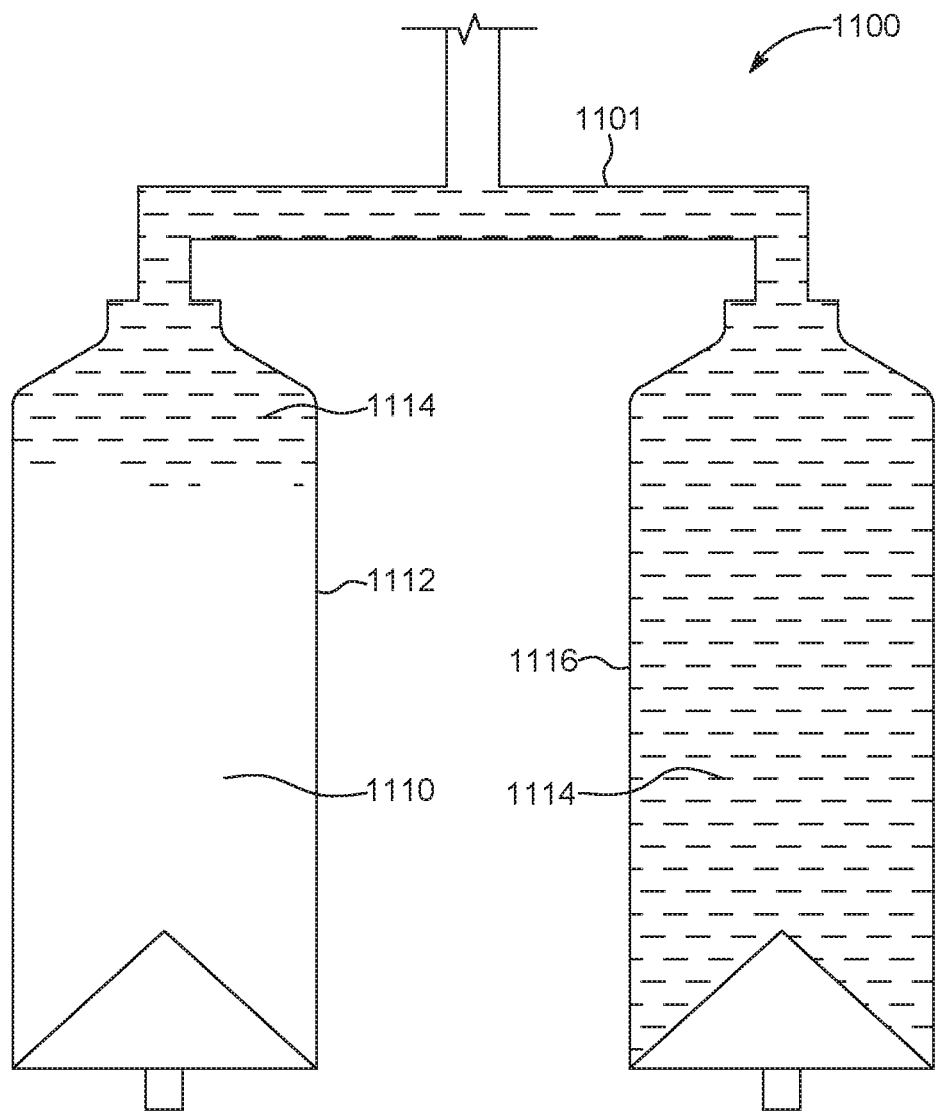
FIG. 7 is a rendering of a portion of a prior art fluid injector system.

FIG. 6A is a graph 1000 showing pressure versus time of a first fluid 1002, such as contrast, and a second fluid 1004, such as saline, wherein the first and second fluids 1002, 1004 develop the same pressure over time. It will be appreciated that when a fluid injector system delivers fluid in accordance with this pressure profile, the likelihood of backflow of one of the first or second fluids 1002, 1004 into a reservoir containing the other of the first or second fluids 1002, 1004 is relatively low and/or zero. Conversely, FIG. 6B is a graph 1010 showing pressure versus time of a first fluid 1012, such as contrast, and a second fluid 1014, such as saline, wherein the first and second fluids 1012, 1014 develop different pressures over time. In fluid injector systems with pressure profiles such as illustrated in FIG. 6B, undesirable backflow is known to occur from the higher pressure contrast reservoir into the lower pressure saline reservoir while there is a pressure differential, ΔP, between the reservoirs. This is depicted most clearly in FIG. 7, which shows a portion of a prior art fluid injector system 1100. As shown, a lower pressure first fluid, e.g., saline 1110, is contained in a first fluid reservoir 1112, and a second fluid, e.g., contrast 1114, and is contained in a second fluid reservoir 1116. Additionally, as shown, a fluid conduit 1101 may provide a fluid pathway between the first and second fluid reservoirs 1112, 1116 during a situation known as dual-flow, wherein both the first and second fluid reservoirs 1112, 1116 are open and a mixture of a specific ratio of contrast and saline flows to the patient line at the same time. As illustrated in FIG. 7, due to a difference in pressure profiles between the first and second fluid reservoirs 1112, 1116, e.g., see FIG. 6B where contrast 1114 corresponds to pressure curve 1012 and saline 1110 corresponds to pressure curve 1014, contrast 1114 from second fluid reservoir 1116 has undesirably "backflowed" and entered first fluid reservoir 1112.

Dual-flow phases can be programmed in volume ratios from, for example, 1% contrast/99% saline to 99% contrast/1% saline. As such, there is a wide range of pressure gradients that may develop between first, saline reservoir and second, contrast fluid reservoir. According to certain flow conditions, backflow may be identified as contrast mixing into the saline reservoir, as the density difference would cause the contrast to sink to the bottom and accumulate over time. In certain embodiments, this type of mixing scenario is common when the dual flow ratio is 95% to 99% contrast to 5% to 1% saline for a dual-flow phase as the contrast flow rate is much higher than the saline flow rate, and therefore generates a greater pressure differential in the contrast reservoir relative to the saline reservoir.

According to various embodiments, the dual-flow phase may be a first programmed phase of the injection, or can follow a contrast phase, saline phase, different dual-flow phase, or a delay phase. Under certain embodiments, a programmed protocol sequence may be a contrast phase, then a dual-flow phase, followed by a saline phase. In this case, the contrast reservoir will be injecting and generate some steady state pressure for the contrast phase. As the dual flow phase begins, the saline reservoir will then open and begin to ramp up pressure as saline flow is initiated. Ramping up pressure in the saline reservoir may include moving the drive component to pressurize the fluid, along with compensating for volume expansion of the reservoir due to compliance uptake and mechanical slack uptake. However, if the saline pressure opens up to the outlet line while at atmospheric pressure or pressure lower than the contrast phase, and the contrast has the greater pressure, such as from the previous phase pressure generated, backflow may occur through the fluid conduit into the saline reservoir while the saline reservoir is ramping to the steady state pressure. To prevent this, one approach is to use pressure equalization, for example by pre-pressurizing the saline reservoir to ensure that at the end of the contrast phase and the start of the dual-flow phase, the pressure in the saline reservoir is substantially equal to the contrast pressure. Since the saline will dilute the contrast during the dual-flow phase, the pressure in the system will drop due to the decreased viscosity of the contrast/saline mixture, relative to the contrast, and there will be no delta in pressure to drive backflow.

In certain embodiments, if the dual-flow phase is the first programmed phase of the injection or follows a saline phase, delay phase, or contrast phase of less than 20 mL of volume, the saline may not have sufficient time to pressure equalize to the contrast pressure. Therefore, the risk of the contrast pressure rising faster than the saline is probable and additional logic must be implemented to prevent backflow. In these embodiments, one way to prevent backflow is to ensure that the saline pressure is higher than the contrast during the transient rise in pressure up to steady state. However, it is difficult to ensure a higher saline pressure for dual-flow ratios greater than 50% contrast as the contrast piston is delivering fluid faster than the saline piston. Another approach may be to use pulsing of the saline drive component to create a turbulent, flow front interface in the fluid conduit to prevent flow of the contrast past the turbulent flow front and into the saline syringe.

According to various embodiments of the present disclosure, to counter this observed backflow between a high pressure and a lower pressure reservoir, a behavior herein referred to as micro-pressure fluctuation or pulsing may be implemented. For example, in accordance with various embodiments of the disclosed concept, an improved fluid injector system 1200 configured to perform an injection protocol is partially shown in FIG. 8. As shown, the fluid injector system 1200 includes a control device 1202 (shown in simplified form) operatively associated with each of two or more drive components 1204, 1205 (partially shown in simplified form in FIG. 8). The drive components 1204, 1205 are configured to pressurize and inject a first fluid (e.g., without limitation, saline 1210) from a first fluid reservoir 1212 through a fluid conduit 1201, and at least a second fluid (e.g., without limitation, contrast 1214) from a second fluid reservoir 1216 through the fluid conduit 1201, the fluid conduit 1201 being in selective fluid communication with the first fluid reservoir 1212 and at least the second fluid reservoir 1216. The control device 1202 includes at least one processor 1203 (shown in simplified form in FIG. 8) programmed or configured to actuate a second drive component 1205 to pressurize and inject the contrast 1214 through the fluid conduit 1201, and while the second drive component 1205 is actuated, actuate a first drive component 1204 to introduce intermittent pulses of the saline 1210 to create a turbulent, flow front interface 1211 between the saline 1210 and the contrast 1214 in the fluid conduit 1201 to prevent backflow of the contrast 1214 through the fluid conduit 1201 into the first fluid reservoir 1210. In other words, the flow front interface 1211 acts as a physical fluid barrier having turbulent flow, preventing backflow of the contrast 1214 into the first fluid reservoir 1212.

In addition, the temporary pulsed increase in the saline flow rate generates increased pressure in the first fluid reservoir 1210, at least temporarily reducing the magnitude of the pressure gradient. Accordingly, when the first drive component 1204 is actuated, a capacitance volume of the first fluid reservoir 1210 increases (due to swelling of the reservoir under pressure) and the pressure of the first fluid increases while no contrast 1214 enters the first fluid reservoir 1210 from backflow past flow front interface 1211 in the fluid conduit 1201. Moreover, during delivery of the intermittent pulses, there may be at least three parameters that may be controlled, such as, for example, pulse interval (e.g., time between pulses, pulse frequency), pulse flow rate (e.g., the flow rate of the pulse, pulse amplitude), and the pulse volume (e.g., the effective duration of the pulse), which are discussed in greater detail herein.

Figure 8:
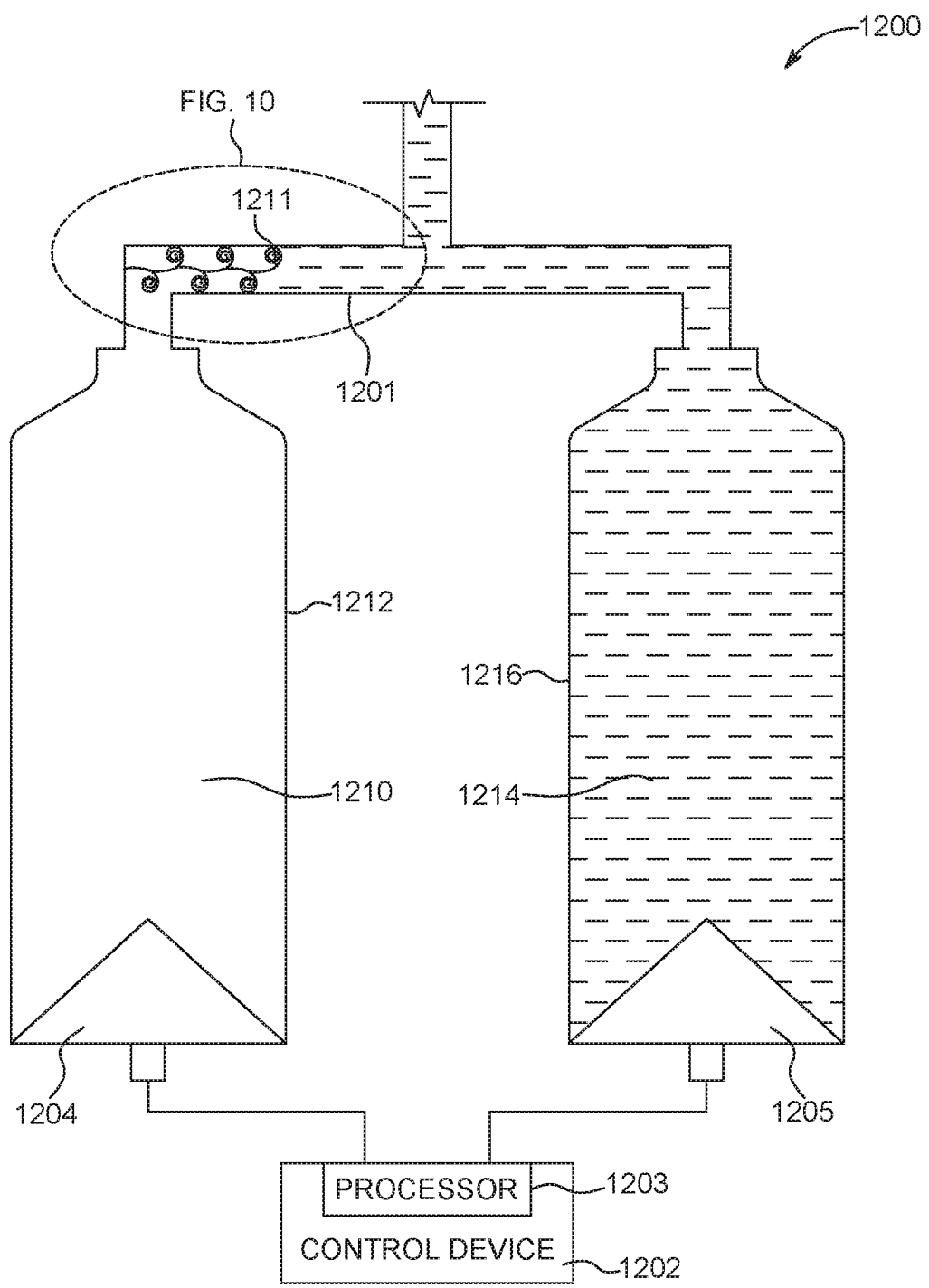
FIG. 8 is a rendering of a portion of a fluid injector system, in accordance with one aspect of the disclosed concept.
Figure 9:
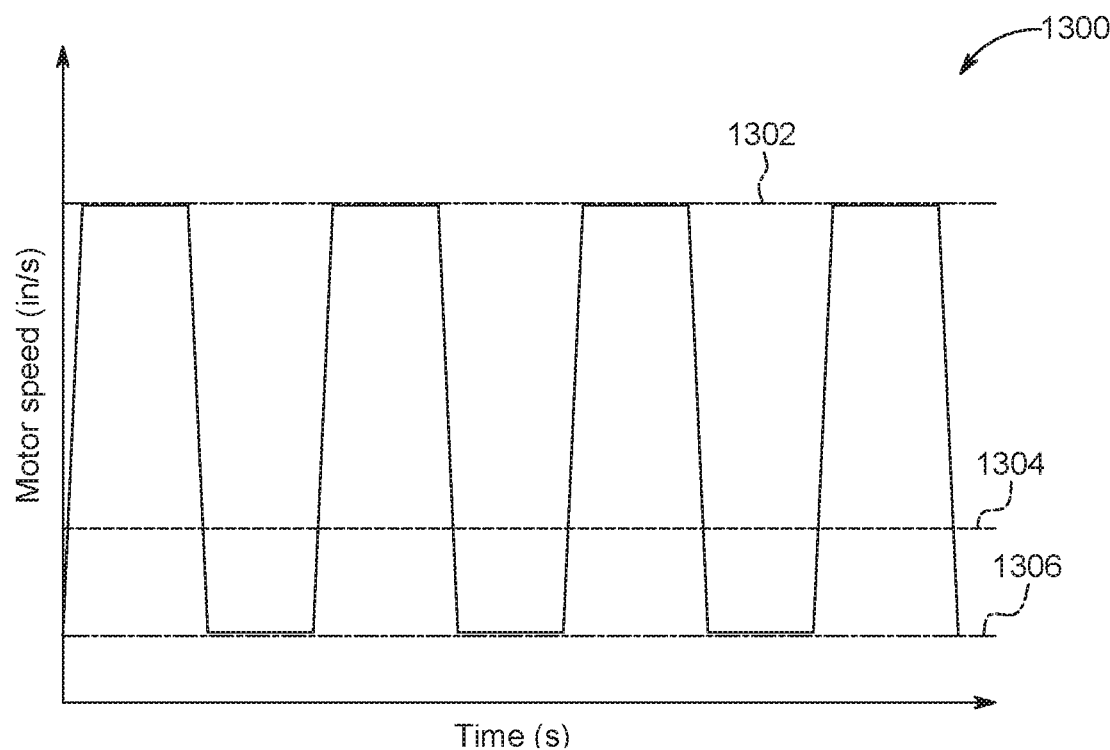
FIG. 9 is a graphical representation of motor speed versus time during a period of operation of fluid injector system of FIG. 8, according to an aspect of the disclosed concept.
Figure 10:
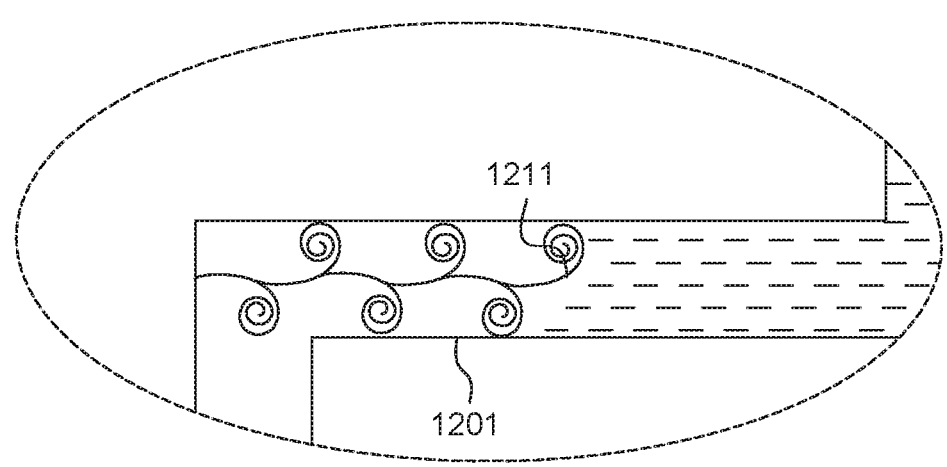
FIG. 10 is an enlarged view of a portion of the fluid injector system of FIG. 8.

FIG. 9 shows a graphical representation 1300 of motor speed versus time during a period of operation of the fluid injector system 1200 (FIG. 8). It will be appreciated that the implementation of micro-pressure fluctuation uses the programmed flow rate of the saline 1210 during a dual-flow phase and introduces intermittent pulses of increased flow rate. These pulses generate turbulent flow in the fluid path at the flow front interface 1211, as well as rapid pressure generation to prevent the backflow from occurring. Accordingly, the micro-pressure fluctuation takes the programmed flow rate and intermittently changes it to generate turbulent flow and higher pressure in the first fluid reservoir 1212 and in certain embodiments, the portion of the fluid conduit 1201 adjacent to the first fluid reservoir 1212 to counter backflow of contrast due to the pressure differential. See, for example, the enlarged view of FIG. 10, which shows the flow front interface 1211 between the saline 1210 and the contrast 1214 in the fluid conduit 1201 as a result of the intermittent pulses of the drive component of the first fluid reservoir 1212.

Referring again to FIG. 8, it will be appreciated that the processor 1203 may actuate the first drive component 1204 to continue to introduce intermittent pulses of the saline 1210 until the pressure of the saline 1210 reaches a pressure that is substantially the same as a pressure of the contrast 1214 (i.e., there is not pressure differential between the first reservoir 1212 and the second reservoir 1216). In one example embodiment, less than 40 milliliters of the saline 1210 may be introduced into the fluid conduit 1201 before the pressure of the saline 1210 reaches the pressure that is substantially the same as the pressure of the contrast 1214. In another example embodiment, less than 25 milliliters of the saline 1210 may be introduced into the fluid conduit 1201 before the pressure of the saline 1210 reaches the pressure that is substantially the same as the pressure of the contrast 1214. The volume of saline 1210 necessary to reach pressure equilibrium may depend, for example on one or more of fluid viscosity, desired dual flow ratio, contrast pressure, speed of drive component, geometry of the fluid path including an attached catheter, and combinations thereof. The processor 1203 may further actuate the first drive component 1204 to introduce intermittent pulses of the saline 1210 at a frequency or amplitude that is one of increasing frequency, decreasing frequency, increasing amplitude, decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and the second fluid, a change in a fluid flow rate or pressure in the fluid conduit, a detection of backflow of the second fluid, a difference in fluid properties of the first fluid and the second fluid, and combinations of any thereof. Additionally, the processor 1203 may decrease the intermittent pulses of the saline 1210 and deliver the saline 1210 at a first fluid flow rate and the contrast 1214 at a second fluid flow rate at a desired ratio of the saline 1210 and the contrast 1214 through the fluid conduit 1201.

The logic for the individual pulsing behavior may be determined from a processor operated algorithm or a lookup table 1400. See, for example, FIG. 11, which shows a portion of a lookup table 1400, based on the input parameters of the dual-flow phase programmed ratio and flow rate. The logic for the individual pulsing behavior may also be determined from a predetermined algorithm which determines a pulsing protocol based on injection parameters, for example inputted by a user and/or stored in a saved injection protocol. Suitable examples of injection parameters include programmed flow rate, programmed volume, contrast type used, flush solution used, dual flow ration, and/or catheter size. Accordingly, when the intermittent pulses of the saline 1210 are introduced, the processor 1203 may select one or more of a pulse interval, a pulse flow rate, and a pulse volume from a lookup table (e.g., the table 1400, shown in FIG. 11) or a predetermined algorithm. Additionally, the table 1400 and/or predetermined algorithm may be stored in a memory device, associated with the processor. According to other embodiments, the processor 1203 may also continuously monitor a rate of change of an injection pressure in the fluid conduit 1201, and in response, adjust at least one of a pulse interval, a pulse flow rate, and a pulse volume of the intermittent pulses based on lookup table 1400 or a predetermined algorithm.

Moreover according to certain embodiments after reaching a steady state flow profile, the processor 1203 may monitor at least one of the pressure in the first fluid reservoir 1212 and the pressure in the second fluid reservoir 1216 during injection of the saline 1210 and the contrast 1214 to determine if a difference between the pressure in the first fluid reservoir 1212 and the pressure in the second fluid reservoir 1216 reaches a first predetermined value after the steady state is achieved. Furthermore, if and when the first predetermined value is reached, the processor 1203 may restart or initiate a new protocol of intermittent pulses of the saline 1210 through the fluid conduit 1201 in order to prevent the contrast 1214 from entering the first fluid reservoir 1212. In certain embodiments, the processor 1203 may continue to monitor an injection pressure in the fluid conduit 1201 and determine whether the injection pressure in the fluid conduit 1201 changes by a second predetermined value. In still other embodiments, the processor 1203 may continue to monitor the difference in the pressure in the first fluid reservoir 1212 and the pressure in the second fluid reservoir 1216 and if the ΔP reaches the first predetermined value for a second time or if the injection pressure in the fluid conduit 1201 reaches the first predetermined pressure for a second time, the processor may again initiate a protocol of intermittent pulsing of the saline drive component until the steady state is reached again. In still other embodiments, the processor 1203 may not need to determine if the first predetermined value for the difference in the pressure in the first fluid reservoir 1212 and the pressure in the second fluid reservoir 1216 is reached, or if a first predetermined value for the pressure in the fluid conduit 1201 is reached before initiating a subsequent pulsing protocol or sequence. According to these embodiments, the processor 1203 may extrapolate and calculate based on a trend of the ΔP of the fluid reservoirs or the pressure in fluid conduit 1201, for example by use of a predictive algorithm, that the values are trending towards the first predetermined value, and may therefore initiate a subsequent pulsing protocol before the first predetermined value is reached based on the calculated trend. It will be appreciated that in suitable embodiments it is not required that a ΔP between first and second fluid reservoirs 1212, 1216 be monitored, but rather a pulsing protocol may be based on measurement of a single injection pressure in a patient line. Additionally, a predetermined pulsing sequence may be identified for a programmed dual-flow ratio, volume, flow rate, and/or any combination of injection parameters.

It is important to note that while the intermittent pulses of saline 1210 are being delivered, the pulse-on flow rate (see, for example, pulse-on flow rate 1302 shown in FIG. 9) is an increase over the programmed flow rate (see, for example, programmed flow rate 1304 shown in FIG. 9) and therefore could potentially result in an over-delivery of the saline 1210 or under-delivery of contrast 1214. In one example embodiment, while the first drive component 1204 introduces intermittent pulses of the saline 1210 to create the flow front interface 1211 between the saline 1210 and the contrast 1214 in the fluid conduit 1201, a total volume of the saline 1210 introduced is less than the sum of a user programmed volume and 15 milliliters. This over delivery of saline is generally not desired from a user perspective since it may require more saline volume then is available or required for the injection. To account for this potential saline over delivery, the pulse-off flow rate (see, for example, pulse-off flow rate 1306 in FIG. 9) for the pulses (e.g., the time that the flow rate is not increased), may reduce the saline flow rate below the programmed flow rate. The reduction in flow rate therefore may counter at least a portion of the periods of increased flow rate, resulting in a saline delivery volume that may be approximately equal to the programmed volume. The net difference between the period over which the pulse-on rate 1302 is used to the programmed flow rate 1304 and the period over which the pulse-off flow rate 1306 is used to the programmed flow rate 1304 identifies the over delivered and under delivered volumes during the micro-pressure fluctuations. For example, in FIG. 9, it will be appreciated that a trapezoid bounded by the depicted curve above the programmed flow rate 1304 during a pulsing sequence represents an amount of saline 1210 delivered, whereas a trapezoid bounded by the depicted curve below the programmed flow rate 1304 during a pulsing sequence represents an amount of saline 1210 not being delivered. Accordingly, theoretical expected over-delivered saline volumes for each protocol may then be calculated, based on an area between the programmed flow rate 1304 and the pulse-on flow rate 1302/pulse-off flow rate 1306 curves. In addition, the intermittent pulses may be optimized to minimize and/or eliminate the over-delivery of saline.

It will also be appreciated that the intermittent pulses may only occur during the first 25 milliliters of injection, which has been identified as one of the portions of injection where backflow is a risk. Additionally, once the fluid injector system 1200 reaches steady state for the injection, the pressure difference between the first fluid reservoir 1212 and the second fluid reservoir 1216 has stabilized. With no pressure difference (ΔP) between the first and second fluid reservoirs 1212, 1216, there is no driving force for backflow and the pulsing may be reduced or even discontinued. However in certain embodiments, atypical injection procedures may occur where an adverse event occurs mid-injection which results in a transient rise in pressure. This could, for example, be caused by an extravasation, kinking of a catheter, kinking of a tubing set, etc. To prevent these mid-injection pressure rises from causing backflow, the fluid injector system 1200 may monitor the pressure during the entire injection in a loop executing a predetermined logic. The predetermined logic may include the following steps: 1) set a counter equal to zero, 2) set a timer for 500 milliseconds, 3) store the current pressure of the system, 4) after the conclusion of the 500 millisecond timer, compare the pressure to the stored system pressure at the start, 5) if the pressure increased by 5 psi or more in that duration, increment the counter by one, if the pressure did not increase by 5 psi or more in that duration, reset the counter to 0, 6) repeat steps 2-5 until the counter reaches 3 or the injection phase ends, 7) if the counter reaches 3, trigger the pulsing behavior to execute for 100 milliseconds, check the pressure every 100 milliseconds, if the pressure has increased by 1 psi, then continue the pulsing for 100 milliseconds. Continue to check pressure until there is not a pressure rise of 1 psi or greater in 100 milliseconds. 5 psi has been identified as a maximum pressure change which the fluid injector system 1200 can experience without backflow occurring. This value, known as a system elasticity, and length of the fluid path conduit, would change from system to system.

This logic ensures that even in an adverse event condition, the system is protecting the saline reservoir from contrast contamination.

Figures 11, 12:
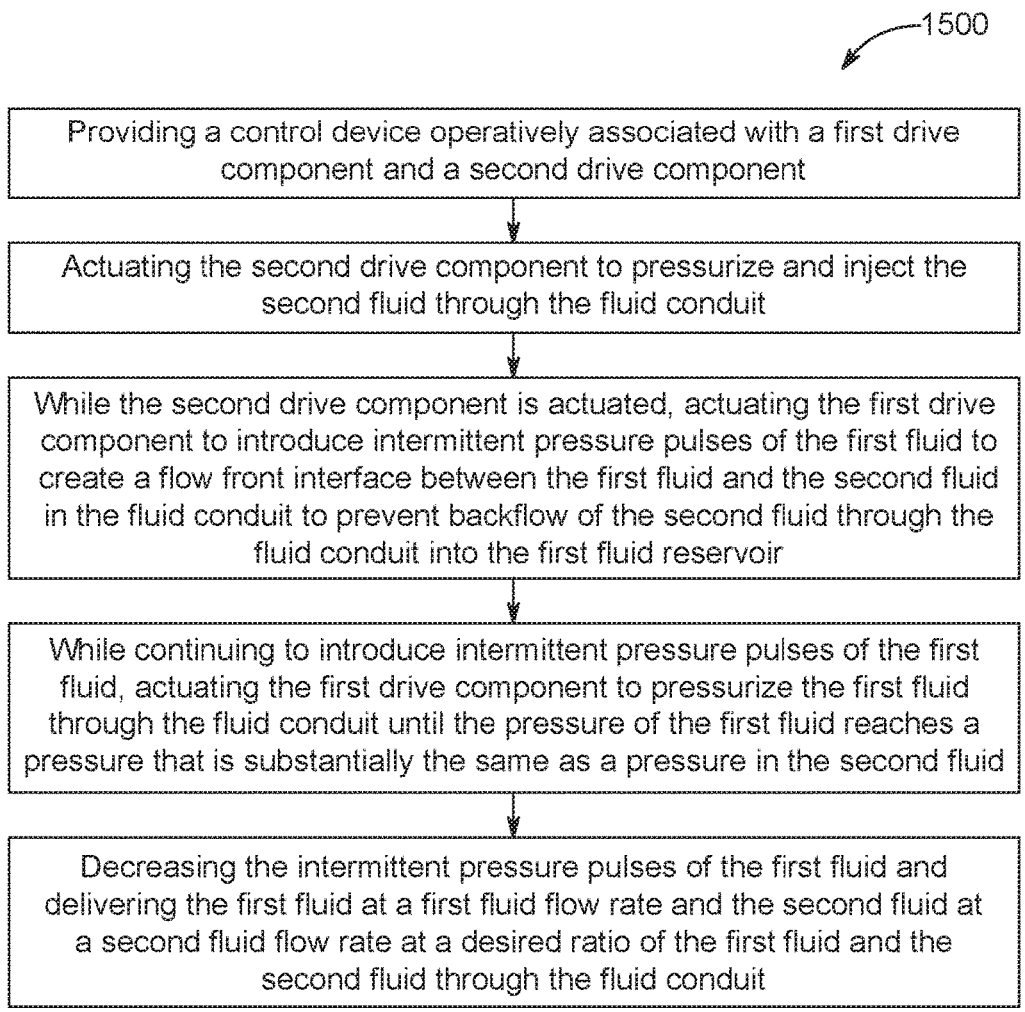
FIG. 11 is a portion of a lookup table, according to an aspect of the disclosed concept.
FIG. 12 is a flow chart of an example method of preventing backflow in a fluid injector system, in accordance with one aspect of the disclosed concept.
Figure 13:
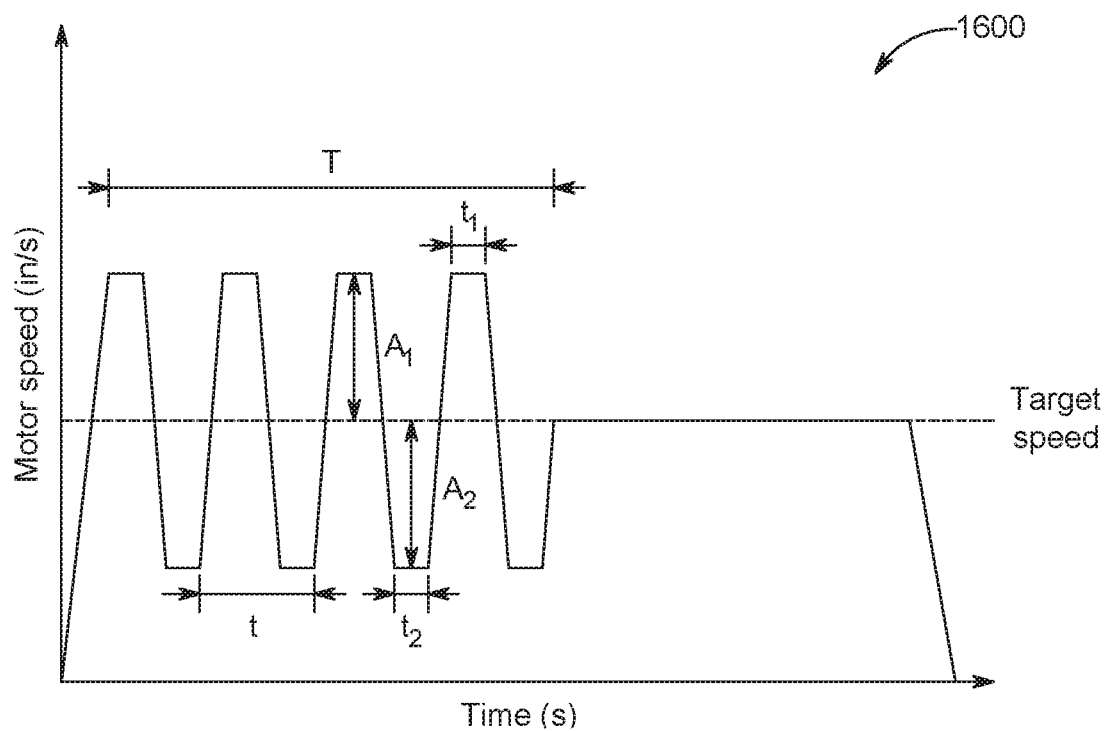
FIGS. 13-18 are other graphical representations of motor speed versus time during periods of operation of the fluid injector system of FIG. 8, according to other aspects of the disclosed concept.
Figure 14:
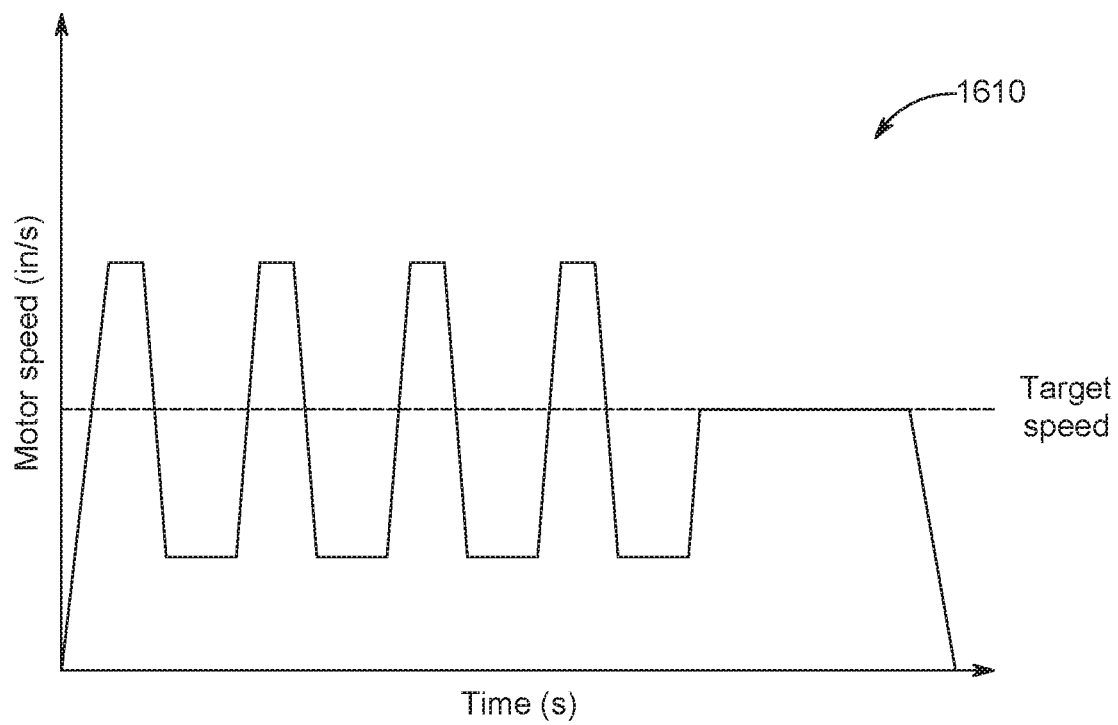
Figure 15:
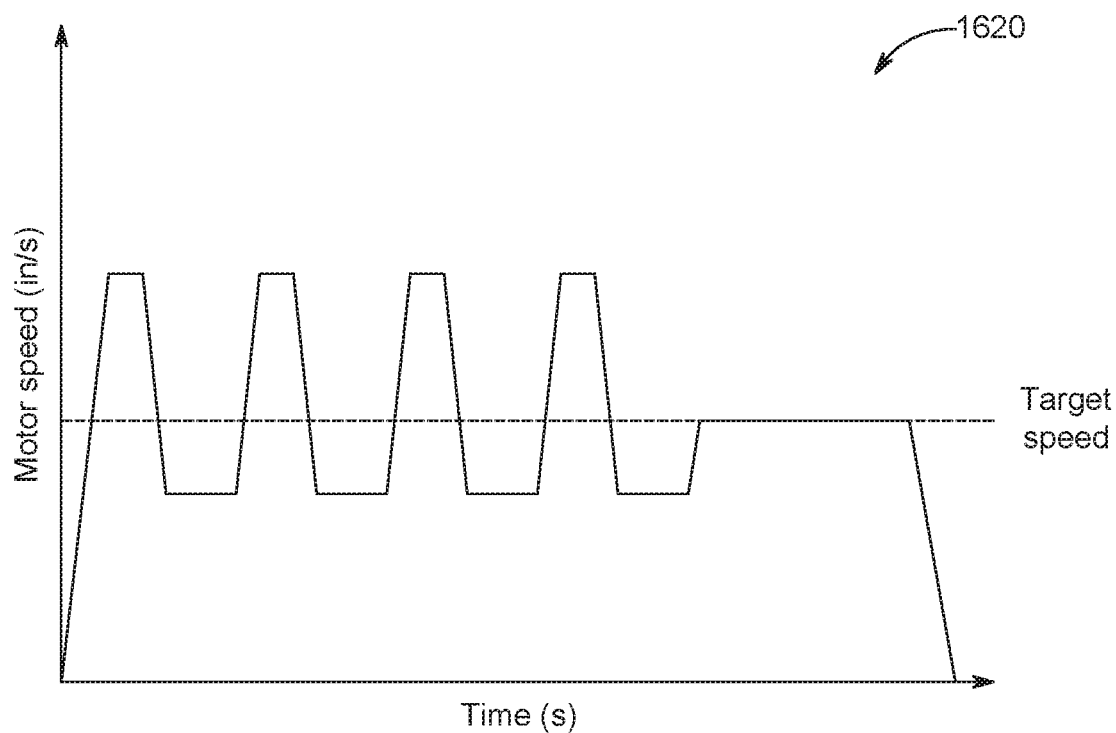
Figure 16:
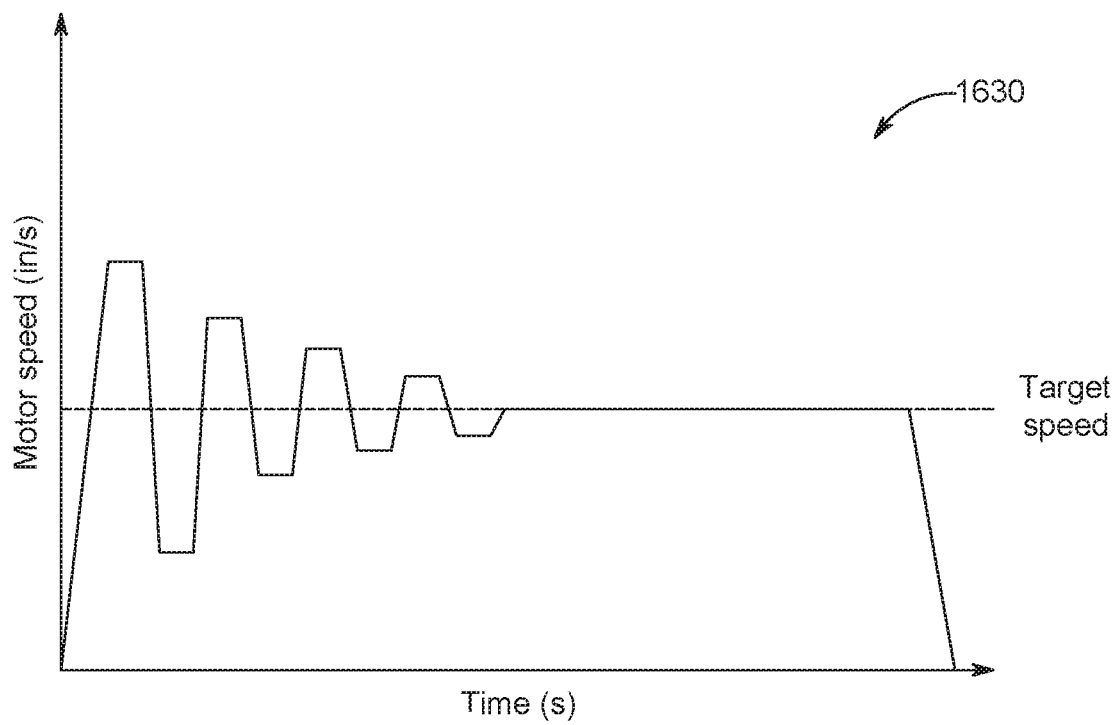
Figure 17:
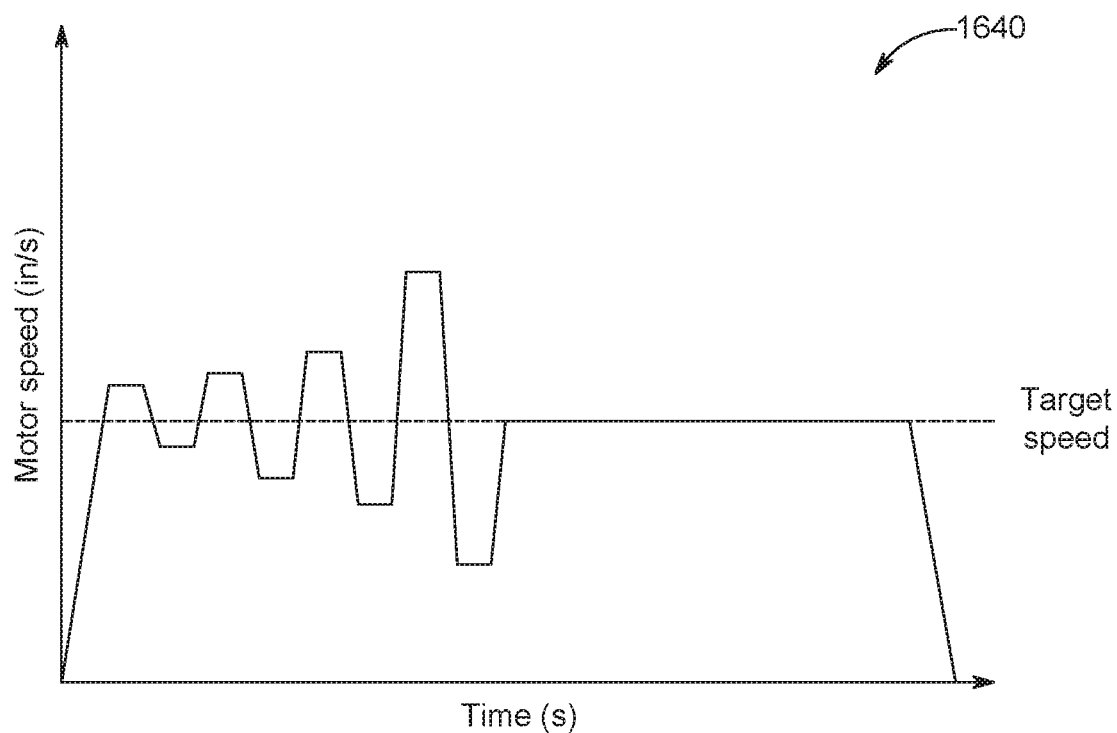
Figure 18:
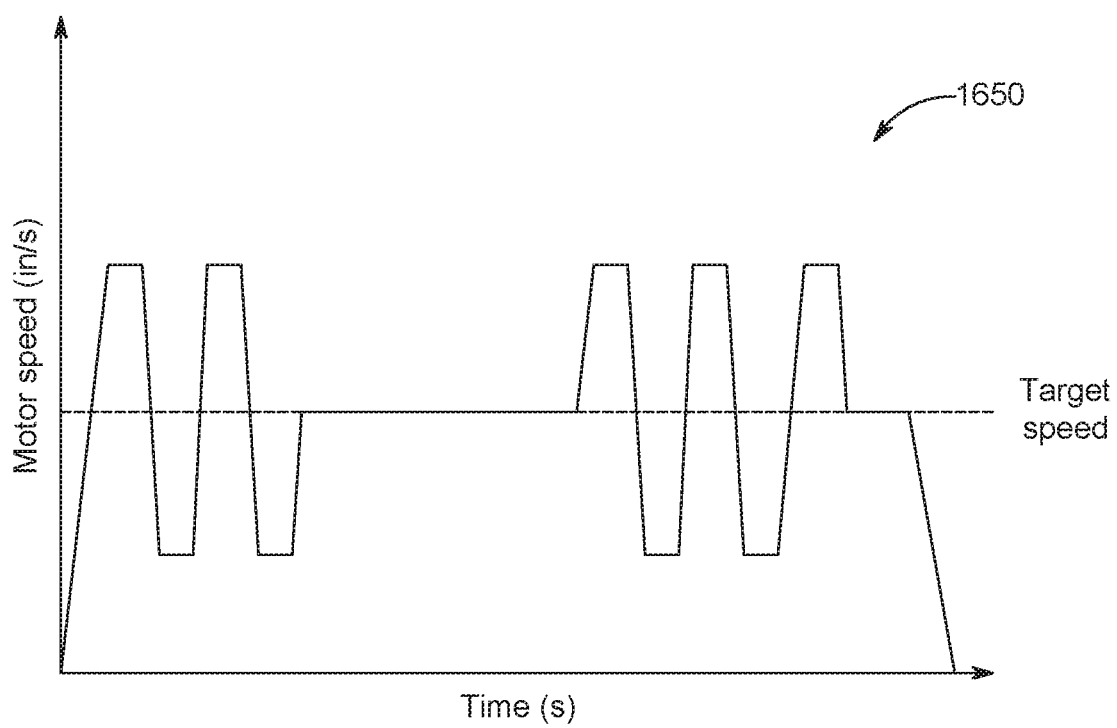
Figure 19:
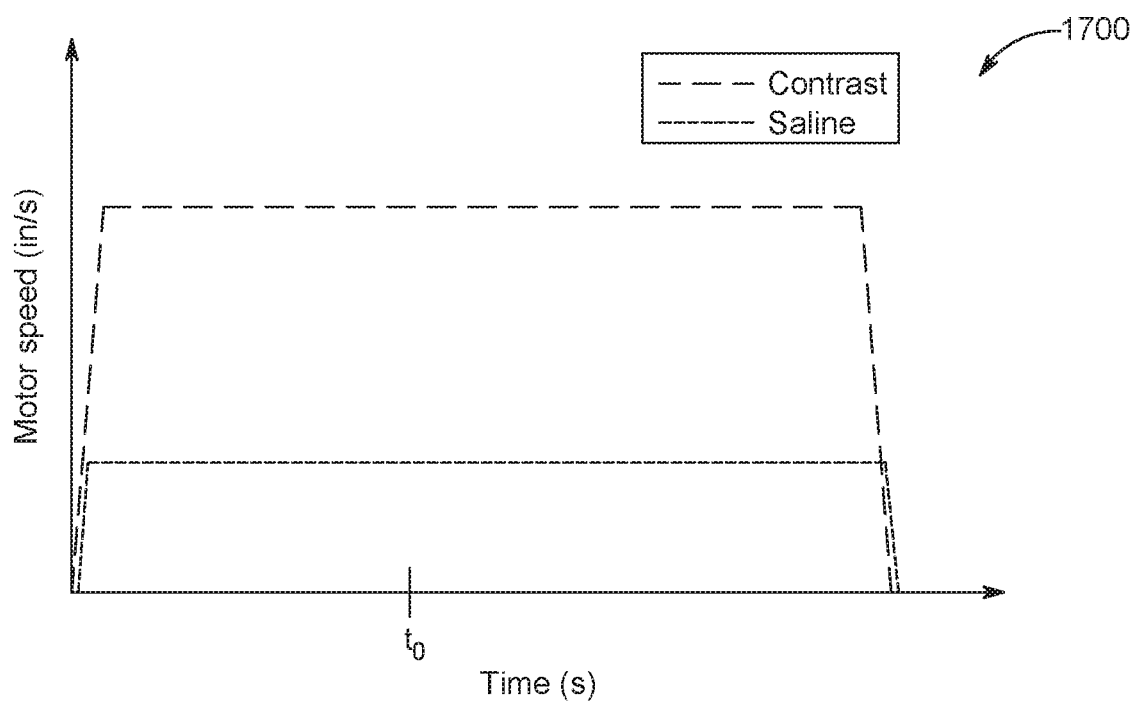
FIGS. 19-25 are other graphical representations of motor speeds, pressure rates, and flow rates for saline and contrast over the course of an injection protocol, in accordance with the disclosed concept.
Figure 20:
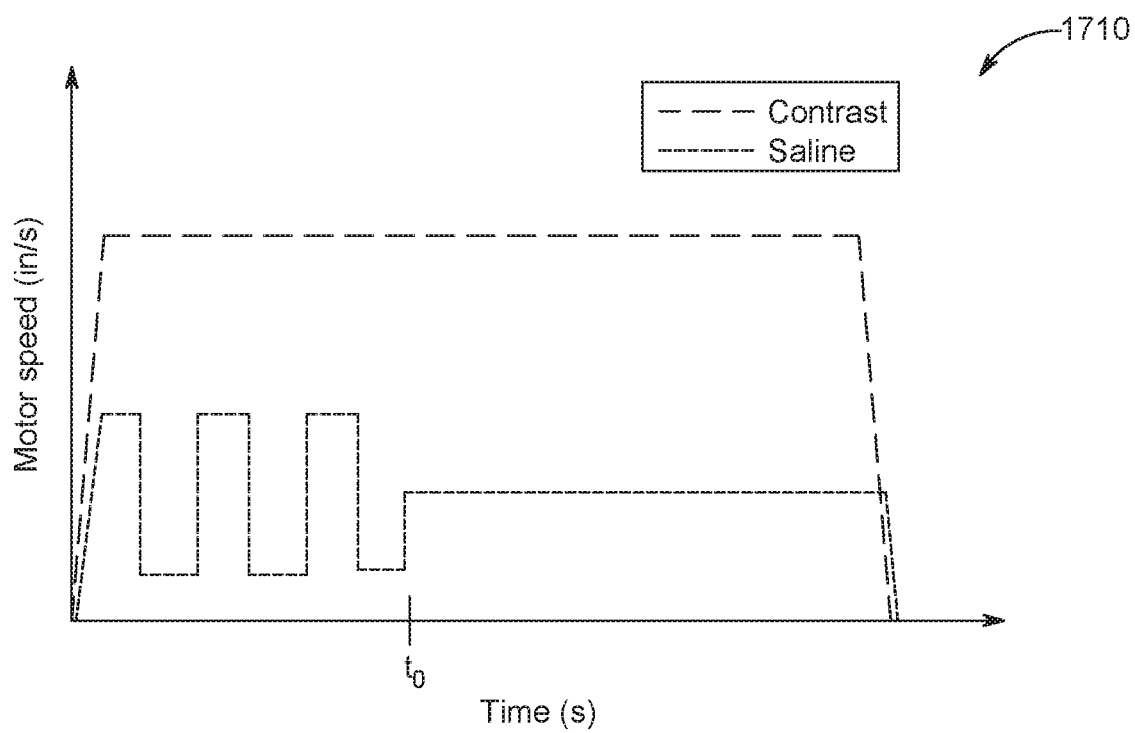
Figure 21:
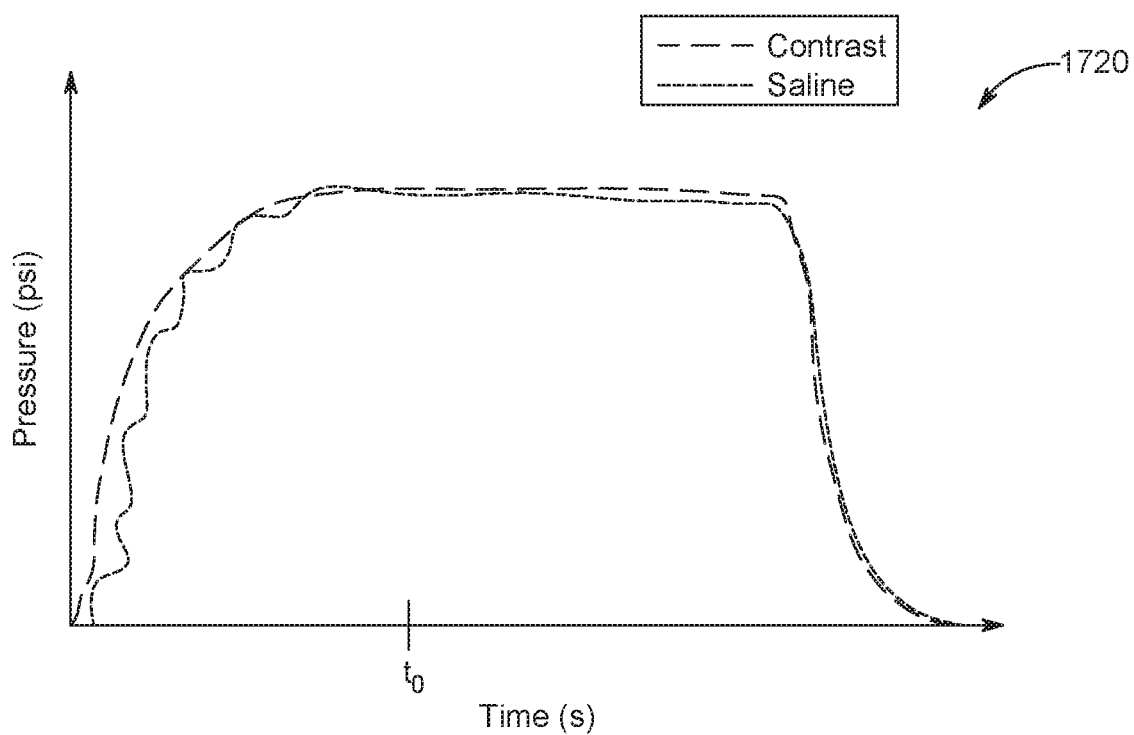
Figure 22:
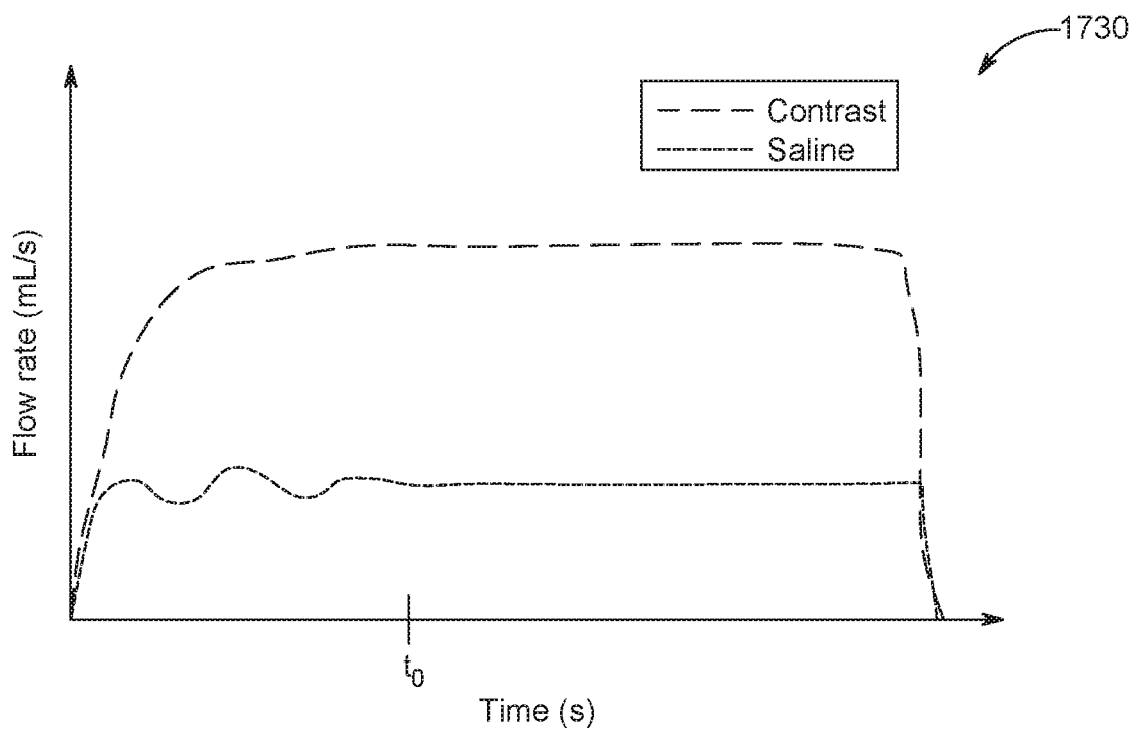
Figure 23:
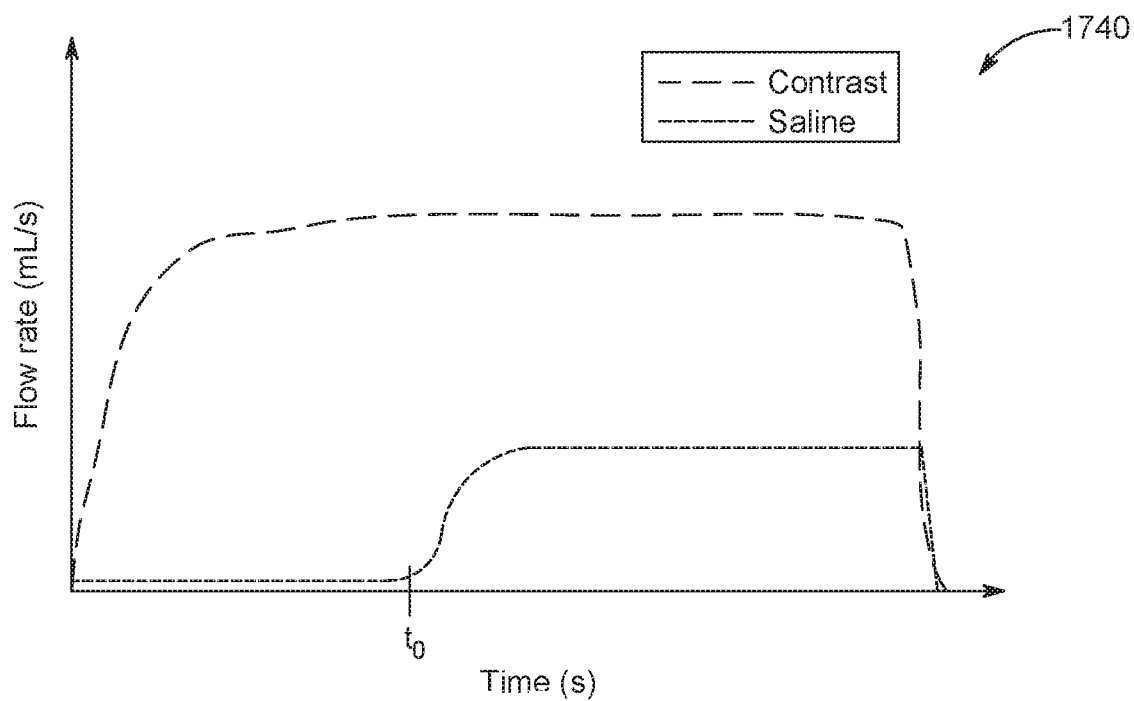
Figure 24:
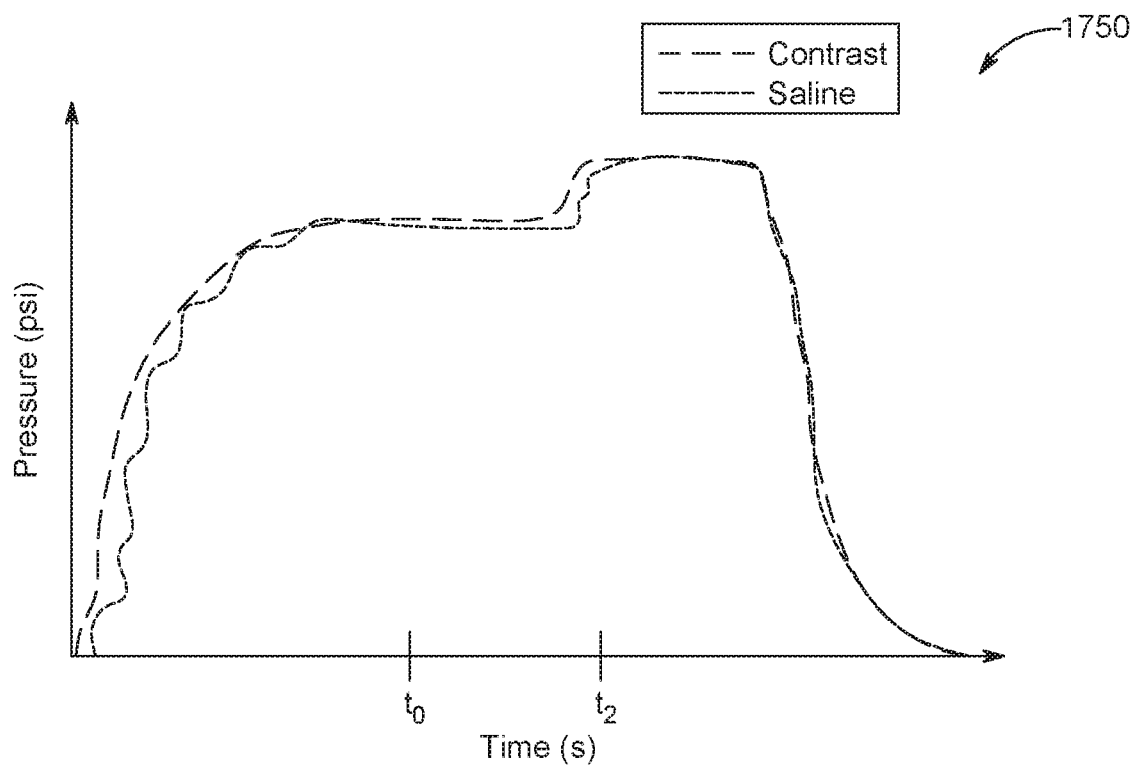
Figure 25:
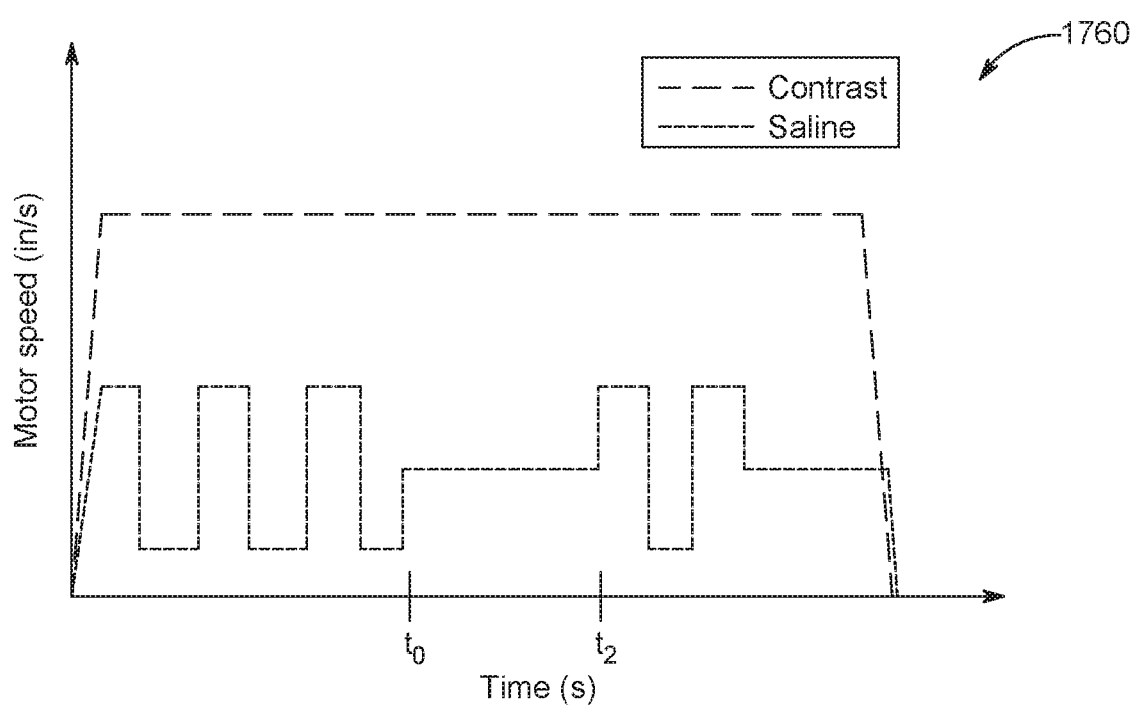

As shown in FIG. 12, according to other embodiments of the present disclosure, a method 1500 is provided for preventing a second fluid from a second fluid reservoir from flowing back into a first fluid reservoir in a fluid injector system configured to perform an injection protocol. The method 1500 may include the steps of providing a control device operatively associated with a first drive component and at least a second drive component, the first drive component configured to pressurize and inject the first fluid through patient fluid conduit, the second drive component configured to pressurize and inject at least a second fluid from the second fluid reservoir through the fluid conduit, actuating the second drive component of the two or more drive components to pressurize and inject the second fluid through the fluid conduit, and while the second drive component is actuated, actuating the first drive component of the two or more drive components to introduce intermittent pulses of the first fluid to create a flow front interface between the first fluid and the second fluid in the fluid conduit to prevent backflow of the second fluid through the fluid conduit into the first fluid reservoir. According to other embodiments, the present disclosure may include methods modified similarly to the various processor initiated steps described herein.

FIGS. 13-18 show various embodiments of graphical representations 1600, 1610 1620, 1630, 1640, and 1650 of motor speed versus time during periods of operation of the fluid injector system 1200 of FIG. 8 using various non-limiting pulsing protocols, according to other aspects of the disclosed concept. It will be appreciated that the behavior of the intermittent pulses can have any combination of parameters. For example, in FIG. 13, t, $t_1$, $t_2$, T, $A_1$, and $A_2$ may correspond to the time between pulses, time over target, time under target, total pulsing duration, amplitude of pulse over target, and amplitude of pulse under target, respectively. As shown in the graphical representations 1610 1620, 1630, 1640, and 1650 of FIGS. 14-18, any and all of these parameters can be modified to produce different pulsing behaviors, sequences, and protocols. Additionally, it will be appreciated that other suitable alternative pulse patterns are contemplated herein. For example and without limitation, graphical representations of pulses having different slopes are contemplated, and pulses may also be more saw-toothed (e.g., less time at full pulse flow). Furthermore, sinusoidal pulse patterns with more rounded apexes are contemplated herein, e.g., as a result of a release of strain on piston components or loss or gain of momentum for the drive components at the start or the end of a pulse.

FIGS. 19-25 show other graphical representations 1700, 1710, 1720, 1730, 1740, 1750, and 1760 of motor speed (FIGS. 19, 20 and 25), pressure (FIGS. 21 and 24), and flow rate (FIGS. 22 and 23) for saline and contrast over the course of an injection protocol, in accordance with an embodiment of the fluid injector system 1200. In each graphical representation 1700, 1710, 1720, 1730, 1740, 1750, and 1760, $t_0$ represents a time at which a pressure in the system reaches steady state, and in graphical representations 1750 and 1760, $t_2$ represents a time at which a pressure delta initiates a second set of intermittent pulses. In graphical representations 1700, 1740, no adjustment has been made to the motor speed, whereas as shown in graphical representations 1710, 1720, and 1730, intermittent pulses of saline have been introduced. Moreover, as shown in graphical representations 1750 and 1760, intermittent pulses of saline have been introduced for a period of time, and at a second, later period of time, a second set of intermittent pulses have been introduced.

In accordance with the disclosed concept, a computer program product may further be provided that includes non-transitory computer readable media having one or more instructions that, when executed by the processor 1203, cause the processor 1203 to actuate the second drive component 1205 to pressurize and inject the contrast 1214 through the fluid conduit 1201, and while the second drive component 1205 is actuated, actuate the first drive component 1204 to introduce intermittent pulses of the saline 1210 to create a flow front interface 1211 between the saline 1210 and the contrast 1214 in the fluid conduit 1201 to prevent backflow of the second fluid 1214 through the fluid conduit 1201 into the first fluid reservoir 1210. According to other embodiments, the present disclosure may include computer program products that may cause a controller to conduct various processor initiated steps described herein.

While examples of fluid injector systems, methods of preventing backflow thereof, and computer program products were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A fluid injector system configured to perform an injection protocol, the fluid injector system comprising:
 a control device operatively associated with each of two or more drive components configured to pressurize and inject a first fluid from a first fluid reservoir through a fluid conduit, and at least a second fluid from a second fluid reservoir through the fluid conduit, the fluid conduit being in selective fluid communication with the first fluid reservoir and at least the second fluid reservoir, the control device comprising at least one processor programmed or configured to:
 actuate a second drive component of the two or more drive components to pressurize and inject the second fluid through the fluid conduit;
 while the second drive component of the two or more drive components is actuated, actuate a first drive component of the two or more drive components to introduce a first set of intermittent pulses of the first fluid to create a turbulent flow in the fluid path at a flow front interface between the first fluid and the second fluid in the fluid conduit to prevent backflow of the second fluid through the fluid conduit into the first fluid reservoir,
 monitor a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value, and
 once the first predetermined value is reached, start a second set of intermittent pulses of the first fluid through the fluid conduit in order to prevent the second fluid from entering the first fluid reservoir.

2. The fluid injector system of claim 1, wherein the at least one processor is further programmed or configured to actuate the first drive component of the two or more drive components to continue to introduce the first set of intermittent pulses of the first fluid until a pressure of the first fluid reaches a pressure that is substantially the same as a pressure of the second fluid.

3. The fluid injector system of claim 1, wherein the at least one processor is further programmed or configured to further actuate the first drive component of the two or more drive components to introduce the first set of intermittent pulses of the first fluid at a frequency or amplitude selected from the group consisting of an increasing frequency, a decreasing frequency, an increasing amplitude, a decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and the second fluid, a change in a fluid flow rate or pressure in the fluid conduit, a detection of backflow of the second fluid, a difference in fluid properties of the first fluid and the second fluid, and combinations of any thereof.

4. The fluid injector system of claim 1, wherein the at least one processor is further programmed or configured to decrease at least one of a frequency and an amplitude of or alter a wave form of the first set of intermittent pulses of the first fluid and deliver the first fluid at a first fluid flow rate and the second fluid at a second fluid flow rate at a desired ratio of the first fluid and the second fluid through the fluid conduit.

5. The fluid injector system of claim 1, wherein the at least one processor is further programmed or configured to monitor an injection pressure in the fluid conduit and determine whether the injection pressure changes by a second predetermined value.

6. The fluid injector system of claim 1, wherein the at least one processor is further programmed or configured to calculate a predetermined injection pressure based on at least one of a programmed injection protocol and user input information, and in response, adjust a pre-set waveform of the first set of intermittent pulses of the first fluid.

7. The fluid injector system of claim 1, wherein the at least one processor is further programmed or configured to continuously monitor a rate of change of an injection pressure in the fluid conduit, and in response, adjust at least one of a pulse interval, a pulse flow rate, and a pulse volume of the first set of intermittent pulses of the first fluid based on a lookup table or a predetermined algorithm.

8. The fluid injector system of claim 1, wherein, when the first set of intermittent pulses of the first fluid are introduced, the at least one processor is further programmed or configured to select at least one of a pulse interval, a pulse flow rate, and a pulse volume from a lookup table or a predetermined algorithm.

9. The fluid injector system of claim 1, wherein less than 40 milliliters of the first fluid is introduced into the fluid conduit by actuation of the first drive component of the two or more drive components before a pressure of the first fluid reaches a pressure that is substantially the same as a pressure of the second fluid.

10. The fluid injector system of claim 1, wherein, while the first drive component of the two or more drive components introduces the first set of intermittent pulses of the first fluid to create the flow front interface between the first fluid and the second fluid in the fluid conduit, a total volume of the first fluid introduced into the fluid conduit is less than the sum of a user programmed volume and 15 milliliters.

11. The fluid injector system of claim 1, wherein, when the first drive component of the two or more drive components is actuated, a capacitance volume of the first fluid reservoir increases and none of the second fluid enters the first fluid reservoir.

12. A fluid injector system configured to perform an injection protocol, the fluid injector system comprising:
a control device operatively associated with each of two or more drive components configured to pressurize and inject a first fluid from a first fluid reservoir through a fluid conduit, and at least a second fluid from a second fluid reservoir through the fluid conduit, the fluid conduit being in selective fluid communication with the first fluid reservoir and at least the second fluid reservoir, the control device comprising at least one processor programmed or configured to:
actuate a second drive component of the two or more drive components to pressurize and inject the second fluid through the fluid conduit;
while the second drive component is actuated, actuate a first drive component of the two or more drive components to introduce a first set of intermittent pulses of the first fluid to create a turbulent flow in the fluid path at a flow front interface between the first fluid and the second fluid in the fluid conduit to prevent backflow of the second fluid through the fluid conduit in to the first fluid reservoir;
continue to introduce the first set of intermittent pulses of the first fluid until a pressure of the first fluid reaches a pressure that is substantially the same as a pressure of the second fluid;
decrease at least one of a frequency and an amplitude of or alter a wave form of the first set of intermittent pulses of the first fluid and deliver the first fluid at a first fluid flow rate and the second fluid at a second fluid flow rate at a desired ratio of the first fluid and the second fluid through the fluid conduit;
either monitor a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value, or monitor an injection pressure in the fluid conduit and determine whether the injection pressure changes by a second predetermined value; and
once a corresponding one of the first predetermined value and the second predetermined value is reached, start a second set of intermittent pulses of the first fluid through the fluid conduit in order to prevent the second fluid from entering the first fluid reservoir.

13. A method of preventing a second fluid from a second fluid reservoir from flowing back into a first fluid reservoir in a fluid injector system configured to perform an injection protocol, the method comprising:
providing a control device operatively associated with a first drive component and a second drive component, the first drive component configured to pressurize and inject a first fluid through a fluid conduit, the second drive component configured to pressurize and inject at least the second fluid from the second fluid reservoir through the fluid conduit;
actuating the second drive component to pressurize and inject the second fluid through the fluid conduit;
while the second drive component is actuated, actuating the first drive component to introduce a first set of intermittent pulses of the first fluid to create a turbulent flow in the fluid path at a flow front interface between the first fluid and the second fluid in the fluid conduit to prevent backflow of the second fluid through the fluid conduit into the first fluid reservoir
monitoring a pressure in the first fluid reservoir and a pressure in the second fluid reservoir during injection of the first fluid and the second fluid to determine if a difference between the pressure in the first fluid reservoir and the pressure in the second fluid reservoir reaches a first predetermined value; and
once the first predetermined value is reached, starting a second set of intermittent pulses of the first fluid through the fluid conduit with the at least one processor in order to prevent the second fluid from entering the first fluid reservoir.

14. The method of claim 13, further comprising actuating the first drive component to continue to introduce the first set of intermittent pulses of the first fluid until a pressure of the first fluid reaches a pressure that is substantially the same as a pressure of the second fluid.

15. The method of claim 13, further comprising actuating the first drive component to introduce the first set of intermittent pulses of the first fluid at a frequency or amplitude selected from the group consisting of an increasing frequency, a decreasing frequency, an increasing amplitude, a decreasing amplitude, and any combination thereof, based on at least one of a difference in pressure in the first fluid reservoir compared to the second fluid reservoir, a difference in an observed ratio of the first fluid and the second fluid compared to a desired ratio of the first fluid and the second fluid, a change in a fluid flow rate or pressure in the fluid conduit, a detection of backflow of the second fluid, a difference in fluid properties of the first fluid and the second fluid, and combinations of any thereof.

16. The method of claim 13, further comprising decreasing at least one of a frequency and an amplitude of or alter a wave form of the first set of intermittent pulses of the first fluid and deliver the first fluid at a first fluid flow rate and the second fluid at a second fluid flow rate at a desired ratio of the first fluid and the second fluid through the fluid conduit.

17. The method of claim 13, further comprising monitoring an injection pressure in the fluid conduit and determine whether the injection pressure changes by a second predetermined value.

18. The method of claim 13, further comprising calculating a predetermined injection pressure based on at least one of a programmed injection protocol and user input information, and in response, adjusting a pre-set waveform of the first set of intermittent pulses of the first fluid.

19. The method of claim 13, further comprising monitoring a rate of change of an injection pressure in the fluid conduit, and in response, adjusting at least one of a pulse interval, a pulse flow rate, and a pulse volume of the first set of intermittent pulses of the first fluid based on a lookup table or a predetermined algorithm.

20. The method of claim 13, further comprising, when the first set of intermittent pulses of the first fluid are introduced, selecting at least one of a pulse interval, a pulse flow rate, and a pulse volume from a lookup table or a predetermined algorithm with the at least one processor.

21. The method of claim 13, wherein less than 40 milliliters of the first fluid is introduced into the fluid conduit by actuating the first drive component before a pressure of the first fluid reaches a pressure that is substantially the same as a pressure of the second fluid.

* * * * *

UNITED STATES PATENT AND TRADEMARK OFFICE
CERTIFICATE OF CORRECTION

PATENT NO. : 12,208,239 B2
APPLICATION NO. : 17/270531
DATED : January 28, 2025
INVENTOR(S) : McDermott et al.

Page 1 of 1

It is certified that error appears in the above-identified patent and that said Letters Patent is hereby corrected as shown below:

In the Specification

In Column 4, Line 18, delete "wave form" and insert -- waveform --, therefor.
In Column 5, Line 49, delete "wave form" and insert -- waveform --, therefor.
In Column 7, Line 46, delete "wave form" and insert -- waveform --, therefor.
In Column 9, Line 32, delete "wave form" and insert -- waveform --, therefor.
In Column 25, Line 56, delete "then" and insert -- than --, therefor.

In the Claims

In Column 29, Line 9, in Claim 4, delete "wave form" and insert -- waveform --, therefor.
In Column 30, Line 18, in Claim 12, delete "wave form" and insert -- waveform --, therefor.
In Column 31, Line 23, in Claim 16, delete "wave form" and insert -- waveform --, therefor.

Signed and Sealed this
Sixth Day of May, 2025

Coke Morgan Stewart
*Acting Director of the United States Patent and Trademark Office*